United States Patent [19]
Lee et al.

[11] Patent Number: 6,015,934
[45] Date of Patent: *Jan. 18, 2000

[54] INDIVIDUALLY WRAPPED ABSORBENT ARTICLE AND METHOD AND APPARATUS FOR ITS PRODUCTION

[75] Inventors: Colin Lee, Oshkosh; Kenneth Triebold, Appleton, both of Wis.

[73] Assignee: Kimberly-Clark Worldwide, Inc., Neenah, Wis.

[ * ] Notice: This patent is subject to a terminal disclaimer.

[21] Appl. No.: 08/995,490

[22] Filed: Dec. 22, 1997

Related U.S. Application Data

[63] Continuation-in-part of application No. 08/968,446, Nov. 12, 1997.

[51] Int. Cl.[7] .................................................. A61F 13/15
[52] U.S. Cl. ............................................ 604/358; 604/387
[58] Field of Search .............................. 270/60; 604/387, 604/358; 493/243, 162; 223/37; 53/52, 203, 285

[56] References Cited

U.S. PATENT DOCUMENTS

| | | |
|---|---|---|
| H1363 | 10/1994 | Leeker . |
| B 516,609 | 2/1976 | Nystrand . |
| 1,731,292 | 10/1929 | Campbell . |
| 1,957,651 | 5/1934 | Joa ............................................ 270/61 |
| 3,031,185 | 4/1962 | Brien . |
| 3,552,736 | 1/1971 | Frick et al. ............................... 270/61 |
| 3,572,689 | 3/1971 | Murphy et al. ........................... 270/70 |
| 3,635,462 | 1/1972 | Joa . |
| 3,698,549 | 10/1972 | Glassman . |
| 3,782,714 | 1/1974 | Spencer et al. ........................... 270/69 |
| 3,905,592 | 9/1975 | Spencer et al. ........................... 270/61 |
| 3,973,567 | 8/1976 | Srinivasan et al. . |
| 3,994,486 | 11/1976 | Nystrand .................................. 270/62 |
| 4,022,456 | 5/1977 | Hooper et al. ........................... 270/65 |

(List continued on next page.)

FOREIGN PATENT DOCUMENTS

| | | |
|---|---|---|
| WO 91/18574 | 12/1991 | European Pat. Off. . |
| WO 89/02729 | 4/1989 | France . |
| 0 324 300 | 7/1989 | France . |
| 5-103814 | 4/1993 | Japan . |
| 7-39820 | 7/1995 | Japan . |
| WO 88/10219 | 12/1988 | Sweden . |
| WO 90/01311 | 2/1990 | United Kingdom . |
| WO 93/09743 | 5/1993 | United Kingdom . |

OTHER PUBLICATIONS

"Sanitary Napkin Positioning Device" Anonymous, Research Disclosure, Mar. 1995.

Product description of Shiseido Feminine Napkin.

*Primary Examiner*—John G. Weiss
*Assistant Examiner*—Miley C. Peppers, III
*Attorney, Agent, or Firm*—Nilles & Nilles, S.C.

[57] ABSTRACT

An individually wrapped absorbent article such as a sanitary napkin which is simple, compact, sanitary, and easy to unwrap for use and to dispose of after use. The absorbent article avoids the need for a separate peel strip and pouch because it is provided with a wrapper that can be folded into a pouch. Substantially the entire backsheet of the absorbent article directly faces the wrapper and is secured to it to form an assembly. In the case of a winged or tabbed type absorbent article, this configuration obviates the need for a separate peel strip to cover the garment adhesive located on the wings or tabs. The assembly is wrapped by folding the lateral flaps thereof longitudinally over one another to enclose the article to prevent the garment adhesive from becoming contaminated. The package is then tri-folded laterally to form an e-shaped pouch. Wrapping and folding are performed by an in-line process that uses simple equipment and that does not require reversal in the direction of article conveyance. Folding is performed by a tri-folding mechanism that translates to convey wrapped packages through an in-line tri-folder assembly and that rotates to fold the packages into the e-shaped pouches.

25 Claims, 14 Drawing Sheets

U.S. PATENT DOCUMENTS

| | | |
|---|---|---|
| 4,084,391 | 4/1978 | Williams, Sr. et al. . |
| 4,508,528 | 4/1985 | Hirsch et al. . |
| 4,556,146 | 12/1985 | Swanson et al. . |
| 4,564,108 | 1/1986 | Widlund et al. . |
| 4,569,672 | 2/1986 | Marion et al. . |
| 4,701,156 | 10/1987 | Larsonneur . |
| 4,717,375 | 1/1988 | Lundmark . |
| 4,743,245 | 5/1988 | Lassen et al. . |
| 4,781,712 | 11/1988 | Barabino et al. . |
| 4,846,824 | 7/1989 | Lassen et al. . |
| 4,846,828 | 7/1989 | Mendelsohn . |
| 4,917,675 | 4/1990 | Taylor et al. . |
| 5,037,417 | 8/1991 | Ternstrom et al. . |
| 5,176,615 | 1/1993 | Munsch . |
| 5,295,988 | 3/1994 | Muckenfuhs et al. . |
| 5,413,568 | 5/1995 | Roach et al. . |
| 5,462,166 | 10/1995 | Minton et al. . |
| 5,569,228 | 10/1996 | Byrd et al. . |

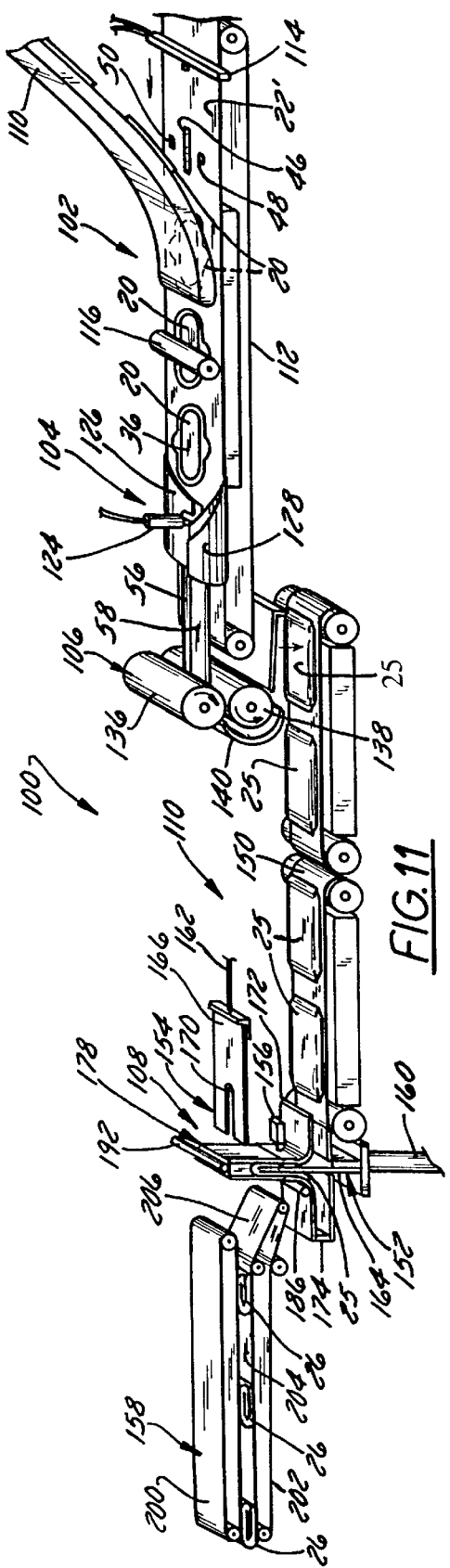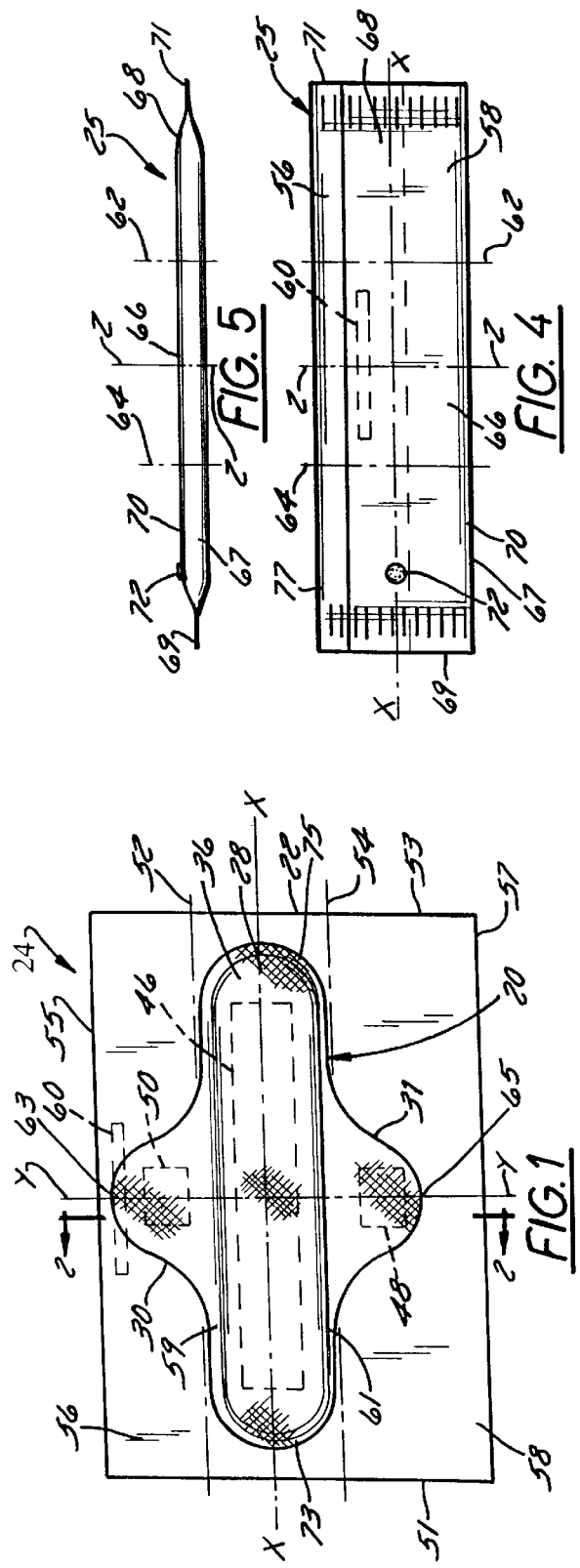

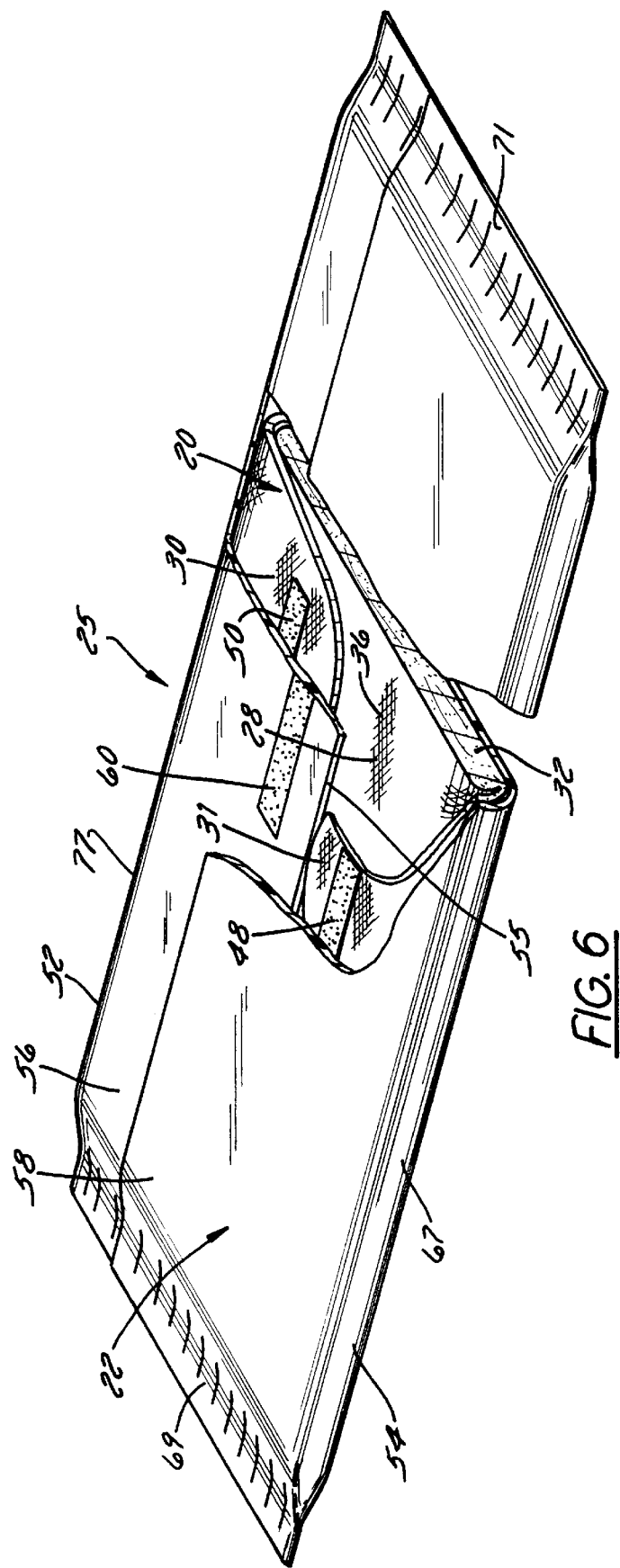

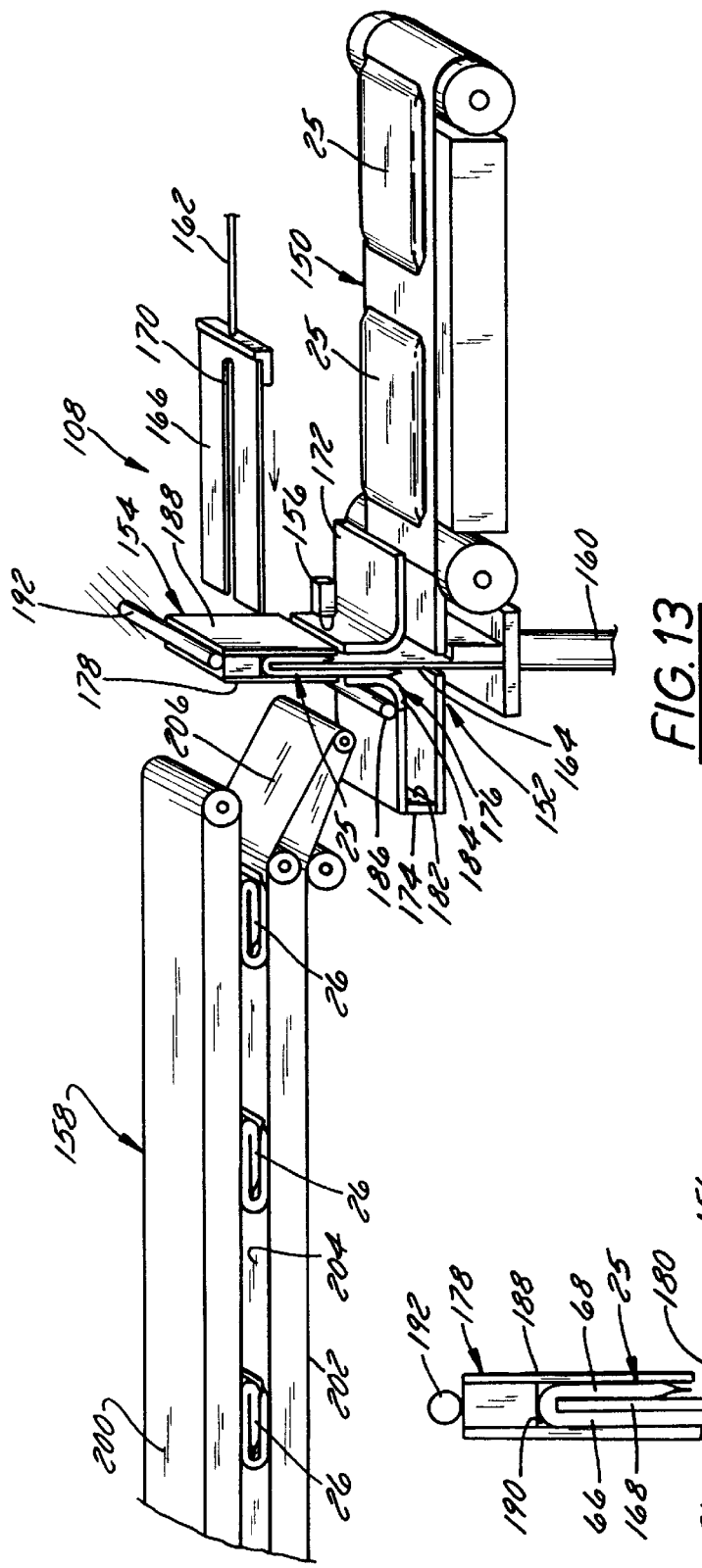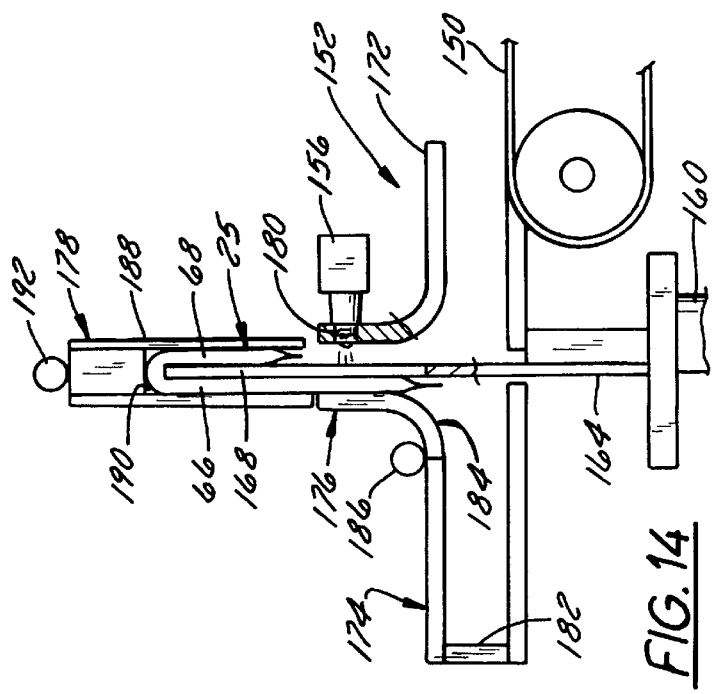

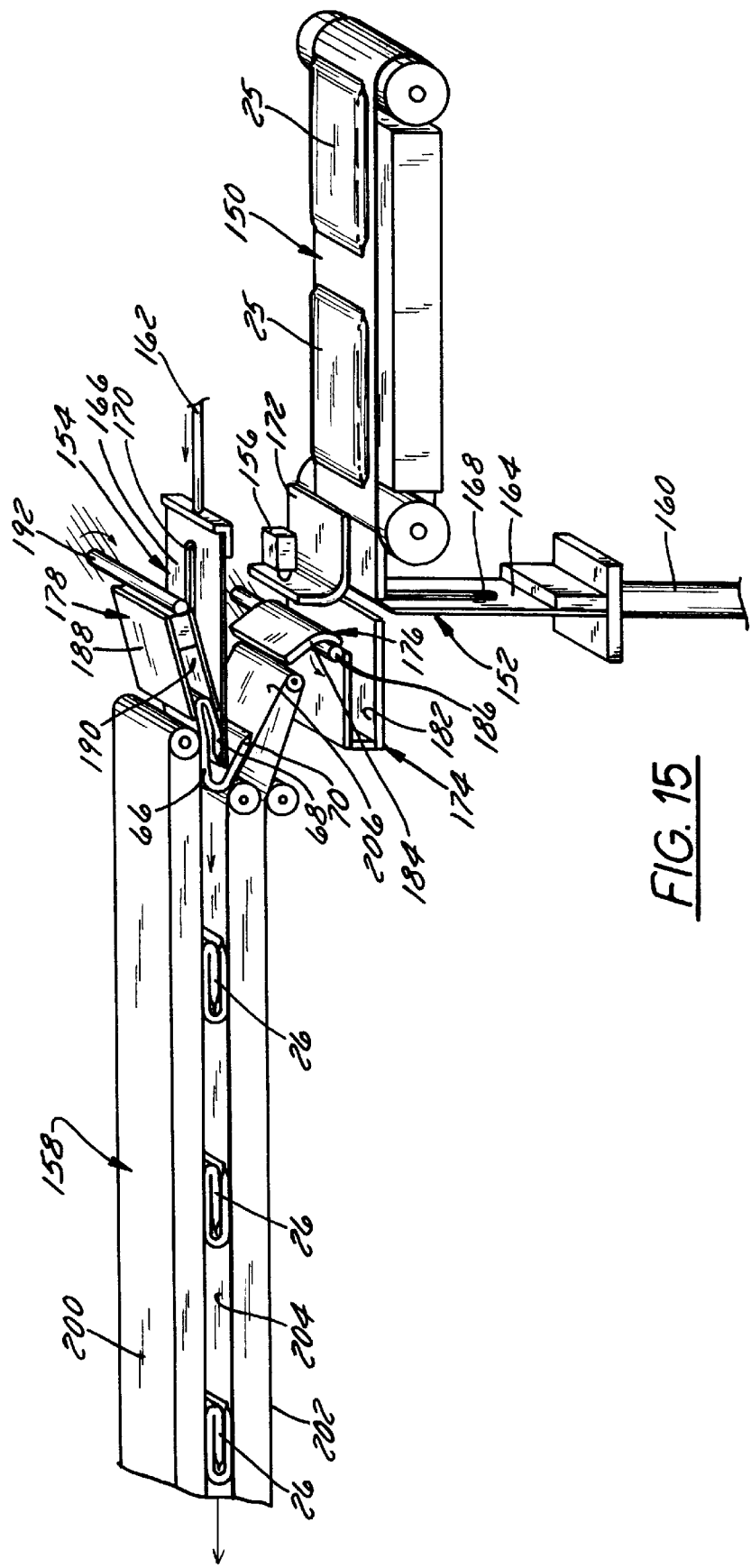

INDIVIDUALLY WRAPPED ABSORBENT ARTICLE AND METHOD AND APPARATUS FOR ITS PRODUCTION

CROSS REFERENCE TO A RELATED APPLICATION

This application is a continuation in-part of co-pending and commonly assigned U.S. patent application Ser. No. 08/968,446, filed Nov. 12, 1997 pending in the name of one of the two co-inventors named in the present application.

BACKGROUND OF THE INVENTION

1. Field of the Invention

This invention relates to absorbent articles such as sanitary napkins, pantyliners, incontinent products or the like and, more particularly, relates to an individually wrapped absorbent article in which the article is releasably secured to a peel strip and folded and sealed to form a package. The package is then wrapped and folded to form a pouch for storing and transporting the absorbent article. The invention additionally relates to a method of wrapping and folding an individually wrapped absorbent article of the aforementioned type and to an apparatus for practicing the method.

2. Discussion of the Related Art

Absorbent articles are well known for absorbing and retaining bodily fluids such as urine, menstrual fluids, blood, etc. Typical of these absorbent articles are sanitary napkins, pantyliners, incontinent products, and the like. The problems addressed by the art will be discussed primarily with reference to sanitary napkins, it being understood that pantyliners, incontinent products, and other absorbent articles also exhibit some or all of these problems.

The two types of sanitary napkins currently in use are a wingless or tabless type that is generally rectangular in shape and a winged or tabbed type that has wings or tabs (hereinafter "wings") extending laterally beyond the lateral edges of the main body of the napkin in a longitudinally central portion thereof. The typical sanitary napkin of either type comprises an absorbent core encased or enclosed within an envelope or sheath that includes a topsheet, also referred to as a "cover," and a backsheet, also referred to as a "baffle." The topsheet is designed to face the user and is liquid-permeable to permit liquid passage to the absorbent core where the liquid is retained. The backsheet is liquid-impermeable. A strip of garment-attachable adhesive is secured on the outer surface of the backsheet to permit releasable or detachable securement of the napkin to a user's undergarment. In the case of a winged or tabbed type napkin, additional adhesive strips or patches are secured to the bottom surface of the wings to permit securement of these wings to the user's undergarment. The adhesive strips can be transferred to the napkins by applying the adhesive to the releasable peel strips, and the adhesive is then transferred to the napkins when the peel strip is attached to the backsheet or baffle. The peel strip protects the adhesive from contamination until the napkins are ready for use, at which time the user removes the peel strips.

Individually wrapped sanitary napkins are desirable for a variety of reasons. For instance, they are compact (e.g., they can be conveniently carried in a consumer's pocket or purse), they prevent the sanitary napkins and the liners from becoming contaminated or soiled prior to use, and used napkins can be disposed of using the pouches or other wrapping materials. Individually wrapped sanitary napkins are disclosed, for example, in U.S. Pat. No. 3,973,567 to Srinivasan et al. (the Srinivasan patent); U.S. Pat. No. 4,556,146 to Swanson et al. (the Swanson patent); and U.S. Pat. No. 5,413,568 to Roach et al. (the Roach patent). All of these patents disclose a sanitary napkin having a backsheet portion adhered to a liner or peel strip that also forms at least part of a wrapper for the napkin. The Srinivasan and Swanson patents disclose individually wrapped wingless or tabless disposable sanitary napkins, whereas the Roach patent discloses an individually wrapped winged or tabbed sanitary napkin.

Conventional individually wrapped sanitary napkins such as those disclosed in the Srinivasan, Swanson, and Roach patents exhibit several drawbacks and disadvantages. For instance, they are relatively difficult to open. In the case of the Swanson patent, the wrapper faces and receives the backsheet portion of the napkin so as to present longitudinal and lateral flaps surrounding the napkin. The napkin and affixed wrapper are then tri-folded as a unit. The lateral edges of the longitudinal flaps are frangibly sealed along their entire length to prevent napkin contamination. These seals must be broken when unwrapping the assembly. This seal breaking requirement hinders unwrapping. In addition, the wrapper is ill-suited for disposal of a used napkin because it is not substantially larger than the napkin.

Napkins of the tabbed or winged type also exhibit additional wrapping challenges. For instance, in the Roach patent, a tabbed or winged type napkin is disclosed which has a backsheet that is releasably adhered to a wrapper similar to the manner in which the Swanson's backsheet is adhered to the corresponding wrapper. However, the ends of the wings extend beyond the lateral edges of the wrapper. The exposed wings are folded longitudinally over the topsheet of the body of the napkin so that the wings are aligned and adjacent to the topsheet of the napkin with their ends facing the longitudinal centerline of the napkin and with their adhesive patches or strips facing upwardly. The wings must be covered with at least one and possibly two separate or dedicated pieces of release liner to protect the adhesive patches on the wings. The additional release liner(s) must be individually removed by the consumer prior to napkin use. This extra step is inconvenient at best and also presents the consumer with at least one additional piece of waste material for disposal. Moreover, because the wrapper is not substantially wider than the body of the napkin, it is rather difficult for the consumer to use the wrapper to dispose of a used napkin.

Another problem associated with conventional individually wrapped sanitary napkins is that production is hindered because wrapping and folding requires a separate process and apparatus and/or because the wrapping and folding operations cannot be performed in-line. Wrapping and folding instead are performed via rather large and complex drum, roll, and striker blade configurations that require at least one and usually several changes in the direction of napkin conveyance during the wrapping and folding processes. Examples of typical processes exhibiting these disadvantages can be found in U.S. Pat. No. 3,635,462 to Joa; U.S. Pat. No. 4,701,156 to Larsonneur; and U.S. Pat. No. 5,176,615 to Munsch.

SUMMARY OF THE INVENTION

It is therefore a principal object of this invention to provide an improved individually wrapped absorbent article that is compact and easy to unwrap.

Yet another object of this invention is to provide an individually wrapped absorbent article that meets at least the first principal object and that can be easily disposed of using the supplied wrapper.

Another object of this invention is to provide an absorbent article that meets the first principal object of this invention and that, in its fully wrapped state, is sanitary but still easy to unwrap.

Still another object of this invention is to provide an individually wrapped absorbent article that meets at least the first principal object and that does not require a separate peel strip as well as a wrapper.

In accordance with a first aspect of this invention, these objects are achieved by providing an individually wrapped absorbent article that comprises an absorbent article and a wrapper. The absorbent article has first and second major mutually opposed faces, and the wrapper has an absorbent article-receiving surface to which at least a portion of the first face of the absorbent article is releasably secured to form an assembly. The assembly has a longitudinal centerline, a lateral centerline, and a perimeter. The perimeter is formed from a pair of opposed lateral edges disposed on opposite sides of the longitudinal centerline and a pair of opposed longitudinal ends disposed on opposite sides of the lateral centerline. The lateral edges are wrapped over the second face of the absorbent article and sealed to form a package.

Preferably, in order to fully-seal the package, a pair of opposed longitudinal ends of the package are each sealed by binding the wrapper to itself.

This invention is applicable to both winged absorbent articles such as winged sanitary napkins and the like and to wingless or tabless absorbent articles such as wingless sanitary napkins, pantyliners, and the like.

Another object of this invention is to provide a package which meets one or more of the foregoing objects and which is folded, rolled, or otherwise manipulated to form a pouch. Preferably, the pouch includes a central portion and first and second longitudinal flaps. The first longitudinal flap is aligned and adjacent to the central portion, and the second longitudinal flap is aligned and adjacent to the first longitudinal flap. The second longitudinal flap preferably is releasably secured to the first longitudinal flap.

Another principal object of this invention is to prove an individually-wrapped winged sanitary napkin that does not require separate peel strips for the wings of the napkin.

In accordance with another aspect of this invention, this object is achieved by providing an assembly formed from an absorbent article and a wrapper. The absorbent article has first and second major mutually opposed faces, includes a main absorbent body having opposed lateral edges, and includes a pair of wings extending laterally outward from the opposed lateral edges. At least a portion of the first face of the absorbent article is releasably secured to an article-receiving face of the wrapper to form the assembly. In order to protect the garment adhesive on the wings while eliminating the need for a separate peel strip on the wings, the portion of the first face that is secured to the wrapper includes at least part of the absorbent body and at least part of each of the wings.

Preferably, the assembly is wrapped to form a package and then folded to form a pouch as discussed above in conjunction with the first primary object.

Another principal object of this invention is to provide a relatively simple and expedient method of wrapping and folding an assembly formed from an absorbent article and a wrapper to which the absorbent article is releasably secured.

Preferably, the assembly has a longitudinal centerline and a perimeter formed from a pair of laterally-opposed side flaps disposed on opposite sides of the longitudinal centerline and a pair of opposed longitudinal ends. This assembly is wrapped and folded to form a pouch by folding the side flaps longitudinally onto the second face of the absorbent article to form a package, and then folding the package laterally to form a pouch. The step of folding the package laterally preferably comprises folding a first longitudinal flap of the package over a central portion of the package so that the first longitudinal flap is aligned and adjacent to the central portion, then folding a second longitudinal flap over the first longitudinal flap so that the second longitudinal flap is aligned and adjacent to the first longitudinal flap. The first and second longitudinal flaps are then releasably secured to one another.

Another object of this invention is to provide a method which meets the second principal object of this invention and which wraps and folds the absorbent articles in an in-line fashion.

In accordance with still another aspect of this invention, this object is achieved by driving a first reciprocating pusher into the package at a location in the vicinity of a lateral fold-line connecting the central portion to the first longitudinal flap, and by driving a second reciprocating pusher into the package at a location in the vicinity of a lateral fold-line connecting the central portion to the second longitudinal flap.

Another object of the invention is provide an improved method of tri-folding a package to form a pouch.

In accordance with another aspect of this invention, this object is achieved by conveying the package along a travel path and, while the package travels along the travel path, rotating a tri-folding mechanism in contact with the package while translating the tri-folding mechanism at least generally along the travel path. This simultaneous rotation and translation folds a first longitudinal flap of the package about a central portion of the package so that the first longitudinal flap is aligned adjacent to the central portion, and folds the first longitudinal flap and the central portion of the package about a second longitudinal flap of the package so that the second longitudinal flap is aligned adjacent to the first longitudinal flap. The second longitudinal flap then is secured to the first longitudinal flap to form the pouch.

The step of folding the first longitudinal flap about the central portion preferably comprises supporting the first longitudinal flap on a folding plate of the tri-folding mechanism while positioning a folding pin of the tri-folding mechanism in the vicinity of a lateral fold-line connecting the central portion to the first longitudinal flap, and rotating the tri-folding mechanism so that the first longitudinal flap moves with the folding plate to fold about the folding pin and the central portion. The step of folding the first longitudinal flap and the central portion of second longitudinal flap about the second longitudinal flap preferably comprises rotating the tri-folding mechanism so that the first longitudinal flap and the central portion move with the folding pin to fold about the folding plate and the second longitudinal flap. The folding plate and the folding pin preferably are withdrawn from the pouch during or after the folding operation by moving the tri-folding mechanism laterally with respect to the travel path while the tri-folding mechanism translates at least generally along the travel path.

Yet another principal object of this invention is to provide an improved system for wrapping and folding individually wrapped absorbent articles.

In accordance with still another aspect of this invention, this object is achieved by providing a first conveyor which is adapted to convey assemblies comprising a wrapper and an absorbent article secured to the wrapper to the system, a second conveyor which is adapted to convey pouches from the system, and first and second pusher assemblies. The first pusher assembly comprises a vertically reciprocating pusher which is adapted to receive the assemblies from the first conveyor and to partially-fold the assemblies. The second pusher assembly is a horizontally reciprocating pusher located in a vertically-spaced relationship with respect to the first conveyor and the first pusher and which is adapted to receive the assemblies from the first pusher and to further fold the assemblies to form the pouches.

Preferably, the first and second pushers are slotted to permit application of an adhesive to the assemblies without interference from the first and second pushers.

Other system components preferably include 1) a package former which releasably secures absorbent articles to a continuous sheet of wrapper material to form the packages, 2) a longitudinal folder which is located downstream of the package former and which folds the continuous sheet longitudinally to form wrapped packages in which lateral edges of the continuous sheet are positioned laterally inwardly of lateral edges of the packages, and 3) a cutter which is located between the longitudinal folder and the first conveyor and which cuts the continuous sheet between the packages.

Still another object of this invention is to provide an improved system for forming a pouch by the in-line folding of a package.

In accordance with yet another aspect of this invention, the system comprises a package support structure defining a travel path for movement of the package through the system, and a tri-folding mechanism which is rotatable and which is translatable with respect to the travel path. The tri-folding mechanism is adapted to engage and tri-fold the package as the package moves along the travel path.

Preferably, the tri-folding mechanism includes first and second spaced-apart folding elements which are adapted to engage mutually opposed major faces of the package. The first and second folding elements may, for instance, comprise an L-shaped folding plate and a cylindrical folding pin, respectively, which are mounted on a rotatable support structure on which the first and second folding elements are mounted. The rotatable support structure preferably comprises a spindle having an axial face on which the first and second folding elements are mounted.

Other objects, features, and advantages of the present invention will become apparent to those skilled in the art from the following section entitled Detailed Description of the Preferred Embodiment and from the accompanying drawings. It should be understood, however, that the Detailed Description and specific drawings, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWINGS

Preferred exemplary embodiments of this invention are illustrated in the accompanying drawings in which like reference numerals represent like parts throughout, and in which:

FIG. 1 is a top plan view of an assembly constructed in accordance with a first preferred embodiment of the present invention and formed from an absorbent article and a wrapper.

FIG. 4 is a plan view of the combination absorbent article and wrapper shown in FIG. 1 and illustrating the assembly in a state in which it is fully wrapped to form a package.

FIG. 5 is a side elevation view of the package of FIG. 4.

FIG. 6 is a partially cut away perspective view of the package of FIGS. 4 and 5.

FIG. 11 is a partially schematic perspective view of a first wrapper/folder system for combining an absorbent article and wrapper to form an assembly, folding the assembly into a package, and then forming the package into a pouch.

FIG. 13 corresponds to FIG. 12 except that it illustrates the two-stage folder assembly in a second stage of its sequence of operation with a cylinder being moved to an up position in which a first reciprocating pusher of the two-stage folder assembly folds a first longitudinal flap of the pouch over a central portion of the pouch.

FIG. 14 is a partially sectional side elevation view of a portion of the two-stage folder assembly of FIGS. 12 and 13 and showing application of an adhesive to the pouch.

FIG. 15 corresponds to FIGS. 12 and 13 and illustrates the two-stage folder assembly in a third stage of its sequence of operation in which a second longitudinal flap of the pouch is folded over the first longitudinal flap.

DETAILED DESCRIPTION OF THE PREFERRED EMBODIMENT

Pursuant to this invention, an individually wrapped absorbent article such as a sanitary napkin, a pantyliner, an incontinent device, or the like is provided which is simple, compact, sanitary, and easy to unwrap for use and to dispose of after use. The absorbent article does not require a separate peel strip or liner and/or pouch because it is provided with a releasable wrapper which serves as a wrapper as well as a pouch. Substantially the entire backsheet or baffle of the absorbent article directly faces the upper surface of the wrapper and is secured to it by a releasable adhesive to form a combination or assembly. In the case of a winged or tabbed type absorbent article, this configuration obviates the need for one or more additional peel strips for the wings or tabs. The assembly is wrapped to form a package and prevent article contamination by longitudinally folding side flaps of the wrapper. The wrapped package is then tri-folded laterally to form an e-shaped pouch. Wrapping and folding can be performed via an in-line process that uses simple equipment and that does not require reversal in the direction of napkin conveyance. The packages preferably are folded by a tri-folding mechanism that rotates as it translates at least generally along a travel path of the package.

This invention is applicable to a variety of individually wrapped absorbent articles including sanitary napkins, pantyliners, incontinent products, and the like. It is particularly well applicable to sanitary napkins for absorbing and retaining menstrual fluids. The invention therefore will be discussed primarily in conjunction with sanitary napkins, it being understood that it applies to other absorbent articles as well.

Figure 7:
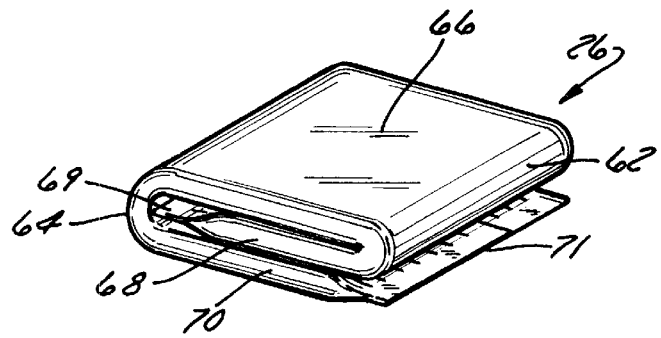
FIG. 7 is a perspective view of a pouch formed by folding the package of FIGS. 4–6.
Figure 2:
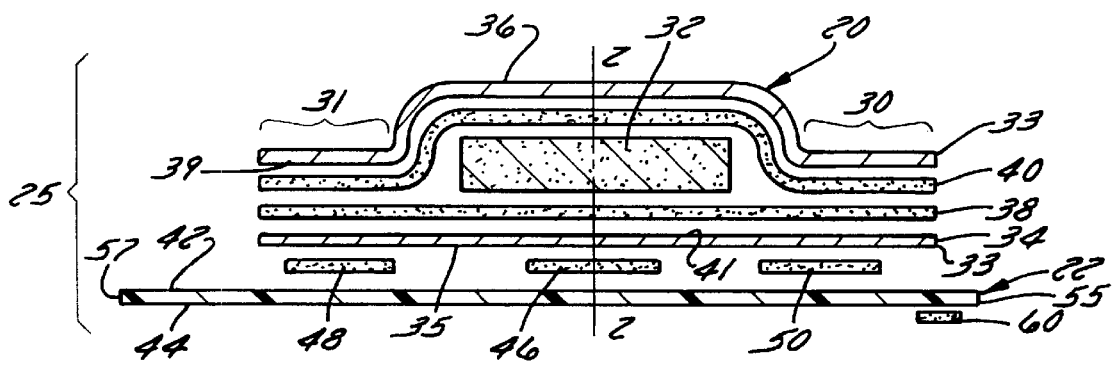
FIG. 2 is a partially exploded sectional elevation view taken generally along the lines 2—2 in FIG. 1.
Figure 3:
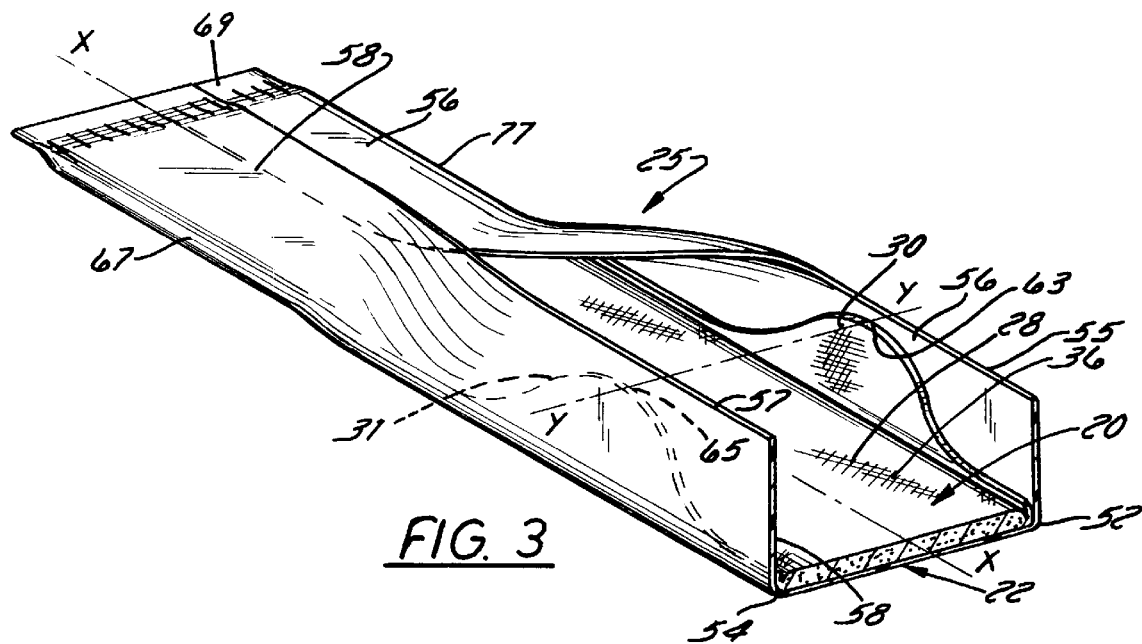
FIG. 3 is a perspective view of the absorbent article and wrapper assembly shown in of FIG. 1 and illustrating the assembly in a partially-wrapped state.

A sanitary napkin 20 is illustrated in FIGS. 1–3 which is releasably secured by adhesion to a wrapper 22 to form an assembly 24. The assembly 24 is folded and sealed to form a package 25 which is best seen in FIGS. 4–6, and the wrapped package is then tri-folded to form a generally e-shaped pouch 26 which is best seen in FIG. 7.

Referring initially to FIG. 1, the sanitary napkin 20 of this embodiment is a winged or tabbed product having a main absorbent body 28 and a pair of laterally-opposed wings or tabs 30 and 31, hereafter referred to as simply "wings". Each of the wings 30 and 31 extends laterally outward from a longitudinally central portion of a respective one of the lateral edges of the main absorbent body 28. As is well known in the art, the wings 30 and 31 are designed for detachable securement to the outer surface of the undergarment of the consumer.

Referring to FIG. 2, the sanitary napkin 20 includes an absorbent core 32 and an envelope 33 encasing the absorbent core 32. The absorbent core 32 may be formed from any suitable absorbent material such as pulp, cellulose wadding, air-felt, layers of tissue paper, superabsorbent materials, or combinations thereof. The envelope 33 includes a liquid-impervious backsheet or baffle 34 which is disposed below the absorbent core 32 and a liquid-permeable topsheet or cover 36 which is positioned above the absorbent core 32. The topsheet 36 is configured to face the user's body and functions to permit liquids to pass through it for retention by the absorbent core 32. The backsheet 34 has a back face 35 which is configured to be releasably secured to the wrapper 22 by three garment adhesive strips or patches 46, 48, and 50. The garment adhesive strips 46, 48, and 50 could be formed from any suitable adhesive and preferably are formed from a pressure-sensitive adhesive of the type commonly used in the art. It should be noted that one or two wide adhesive strips could be used in place of three narrower adhesive strips 46, 48, and 50. Once the wrapper 22 is removed from the napkin 20, the garment adhesive strips 46, 48, and 50 remain with the napkin 20 and function to attach and hold the napkin 20 in position on the inner surface of the user's undergarment. The topsheet 36 is secured to the backsheet 34 by a construction adhesive 38 located on the inner surface 39 of the topsheet 36 and a bodyside layer of construction adhesive 40 on the inner or front face 41 of the backsheet 38. This construction adhesive 40 could be eliminated in favor of a thermal bond if desired or by other bonding techniques known to those skilled in the art, such as ultrasonics.

The sanitary napkin 20 per se is conventional. However, its relationship with the wrapper 22 and the package pouch 26 formed by wrapping and folding the assembly 24 (see FIG. 7) formed by the napkin 20 and wrapper 22 combination is not. This relationship will now be explained.

Referring again to FIG. 2, the releasable wrapper 22 could conceivably comprise a multi-ply or multi-component arrangement but preferably comprises a single sheet that serves as both a wrapper and as a releasable peel strip. The wrapper 22 may be formed from any suitable thermoplastic such polyethylene or polypropylene, with polyethylene being preferred. The wrapper 22 has first and second opposed major surfaces 42, 44 respectively, with the first or inwardly-orientated surface 42 preferably being coated with a suitable release material to facilitate separation from the adhesive strips 46, 48, and 50. The adhesive strips 46, 48, and 50 could take many configurations so long as they secure both the main absorbent body 28 and the wings 30 and 31 to the wrapper 22. The adhesive strips 46, 48, and 50 permit securement of the main absorbent body 28 and the wings 30 and 31 to the user's undergarment after the napkin 20 is peeled away and removed from the wrapper 22. The three adhesive strips 46, 48, and 50 are relatively long narrow strips. The first or middle strip 46 is aligned along the longitudinal centerline X—X of the main absorbent body 28 (FIG. 1) and extends a substantial percentage of the longitudinal length of the napkin 20. For example, the adhesive strips 46, 48, and 50 can extend about 50% to about 99% of the full length of the napkin 20. The second and third strips 48 and 50, respectively, are each disposed beneath a generally central portion of the respective wings 30 and 31. It is important to note that the second and third adhesive strips 48 and 50 serve to secure the wings 30 and 31 to the wrapper 22. This obviates the need to fold the wings 30 and 31 back over the main absorbent body 28 and to protect the adhesive strips 48 and 50 via a separate peel strip.

Referring again to FIG. 1, the releasable wrapper 22 has a perimeter defined by a pair of longitudinal ends 51 and 53 disposed on opposite sides of the lateral centerline Y—Y and a pair of lateral edges 55 and 57 disposed on opposite sides of the longitudinal centerline X—X. Preferably, the lateral edges 55 and 57 of the wrapper 22 extend outwardly beyond the respective lateral side margins of the sanitary napkin 20 so that lateral spaces are formed between outermost lateral ends 63 and 65 of the wings 30 and 31 and the edges of the wrapper 22. The lateral edges 55 and 57 of the wrapper 22 preferably extend about 1.5" to 2.5", and even more preferably about 2.0", beyond the corresponding lateral edges 59 and 61 of the main absorbent body 28. The lateral edges 55 and 57 of the wrapper 22 also extend between about 0.25" and 0.75", and even more preferably about 0.5", beyond the ends 63 and 65 of the wings 30 and 31. The longitudinal ends 51 and 53 of the wrapper 22 similarly extend beyond longitudinal ends 73 and 75 of the napkin 20. This configuration not only facilitates securement of the napkin 20 to the wrapper 22 but also ensures that enough wrapper material is available to permit disposal of a used napkin 20 in it.

The combination of the napkin 20, being releasably secured to the wrapper 22, is folded and sealed to form a package 25 (FIGS. 3–6). The package 25 is then folded to provide a sanitary, compact, easy to handle and easy to unwrap pouch 26 (see FIG. 7).

Specifically, referring to FIG. 3, the assembly 24 is folded longitudinally about two longitudinally-extending fold lines 52 and 54, so that a side flap 56 and a side flap 58 extend laterally from the lateral edges 55 and 57 of the wrapper 22. The side flaps 56 and 58 rest on the topsheet 36 of the napkin 20 after folding as seen in the left half of FIG. 3. This wrapping protects lateral edges 67 and 77 of the package from contamination and obviates the need to seal the edges of the package 25, thereby facilitating production and also facilitating use, to the extent that there is no need to break a seal running the length of the package 25 when unwrapping the napkin 20. Preferably, the longitudinal fold lines 52 and 54 are coextensive with the longitudinal sides or edges 59 and 61 of the napkin 20 and are located such that the side flap 58 overlaps the other side flap 56 in the vicinity of the longitudinal centerline X—X of the package 25 as seen in FIG. 4, thereby completely covering the napkin's topsheet 36. The side flaps 56 and 58 may be secured to one another by adhesive 60 in the form of one or more adhesive dots or strips (see FIGS. 2 and 4) to facilitate subsequent folding and to provide a more compact package 25. However, there is no need to apply the adhesive strip 60 along the entire length of the overlap even in those instances in which the adhesive strip 60 is utilized.

Ends 69 and 71 of the package 25 also are preferably sealed as seen in FIGS. 4–6 to fully enclose the napkin. The wrapped package 25 is folded laterally (i.e., parallel to the lateral centerline Y—Y in FIGS. 4 and 5) about laterally-extending fold lines 62 and 64 to form a pouch 26 (FIG. 7) having a central portion 66 and first and second longitudinal flaps 68 and 70. The first flap 68 is positioned adjacent to and below the central portion 66, and the second flap 70 is positioned adjacent to and below the first flap 68, as illustrated in FIG. 7, to form a generally e-shaped pouch.

The second flap 70 is frangibly secured to the first flap 68 to prevent the pouch 26 from unintentionally unfolding. The securement could be accomplished by use of an adhesive 72 (best seen in FIGS. 4 and 5), such as dots or a strip of adhesive tape extending from the outer end 71 of the second flap 70 to the inner end of the first flap 68 forward by the fold line 62. As illustrated, the securement is achieved by application of an adhesive spot 72 (hereafter a "patch") of a pressure sensitive adhesive positioned between the first and second flaps 68 and 70 at a location near the outer end 71 of the second flap 70.

The finished wrapped and folded pouch 26 is extremely sanitary because the napkin 20 is essentially completely sealed from the environment. The pouch 26 also is quickly and readily opened and unwrapped simply by pulling the second flap 70 away from the first flap 68, against the relatively small resistance of the frangible adhesive patch 72. The side flaps 58 and 56 are then unfolded against the relatively slight resistance of the frangible adhesive strip 60. The napkin 20 can now be peeled away from the wrapper 22 simply by grasping one end of the napkin 20 and pulling it longitudinally with respect to the wrapper 22. There is no need to touch any sanitary portions of the napkin 20. Nor is there any need to remove separate peel strips that otherwise would be required to cover the adhesive strips 48 and 50 positioned over the wings 30 and 31. The napkin 20 is now ready for attachment to an undergarment. After use, the napkin 20 can be conveniently disposed of by simply wrapping it in the wrapper 22. This wrapping and subsequent disposal are facilitated by the fact that the wrapper 22 is substantially larger than the napkin 20 in both the longitudinal and lateral directions. There is also no need to open a separate pouch to remove the napkin for use or to force a used napkin in a separate preformed pouch during disposal. Unwrapping and disposal thereby are significantly facilitated when compared to many prior art products.

Figure 8:
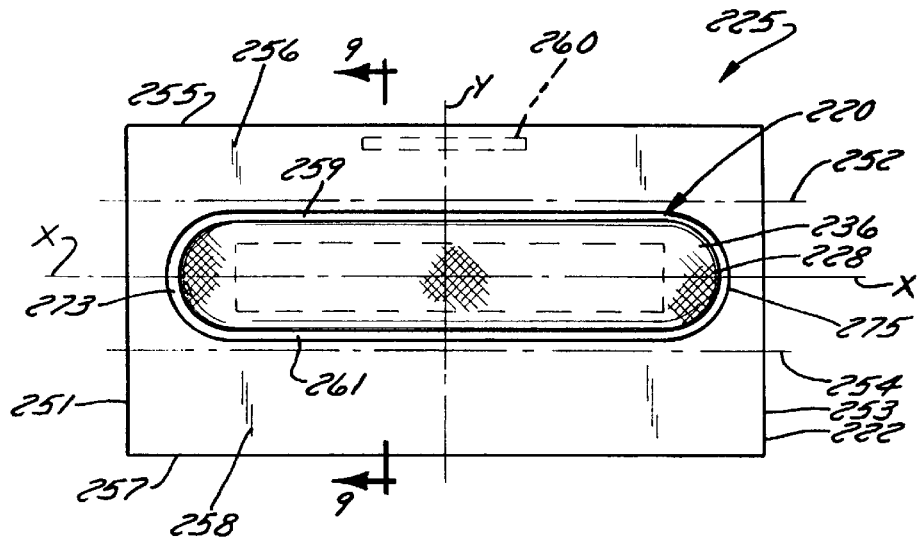
FIG. 8 is a top plan view of an assembly constructed in accordance with a second preferred embodiment of the present invention and formed from an absorbent article and a wrapper.
Figure 10:
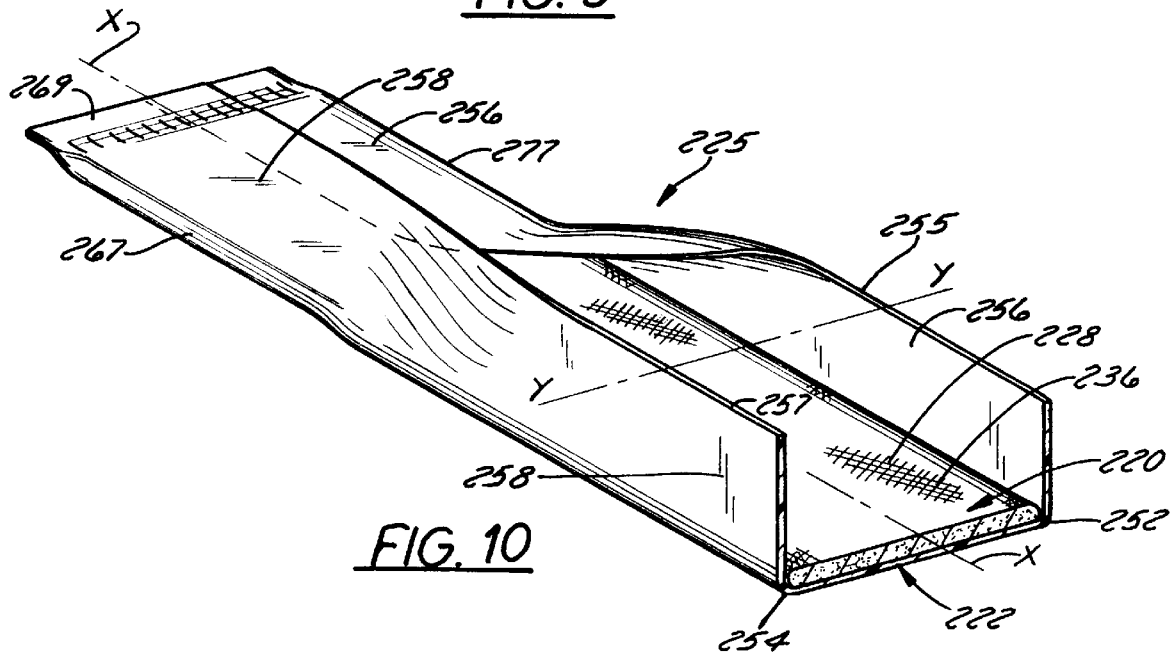
FIG. 10 is a perspective view of the combination absorbent article and wrapper shown in of FIG. 8 and illustrating the combination in a partially-wrapped state.

The invention is also applicable to wingless absorbent articles such as a wingless sanitary napkin 220 illustrated in FIG. 8. The napkin 220 is releasably secured by adhesion to a wrapper 222 to form an assembly 224. The assembly 224 is folded and sealed to form a package 225 which is best seen in FIG. 10, and the wrapped package is then tri-folded to form a generally e-shaped pouch.

Figure 9:
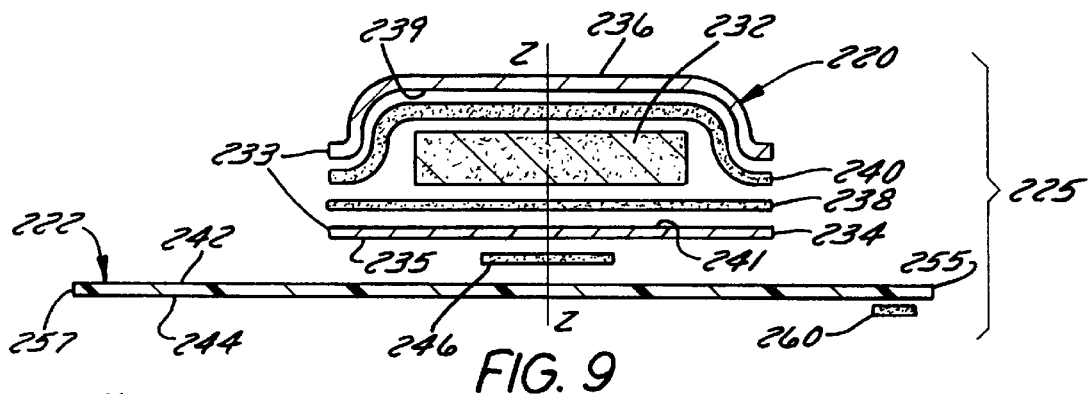
FIG. 9 is a partially exploded sectional elevation view taken generally along the lines 9—9 in FIG. 8.

Referring to FIG. 8, the sanitary napkin 220 of this embodiment has a main absorbent body 228 that is generally rectangular in shape and that has a pair of opposed lateral edges 259 and 261 and a pair of opposed longitudinal ends 273 and 275. "Generally rectangular" as used herein should be construed to encompass oval shapes, hourglass shapes, and the like in addition to encompassing a true rectangular shape. The releasable wrapper 222 has a first or article-receiving surface 242, a second surface 244 (best seen in FIG. 9), and a perimeter defined by opposed longitudinal ends 251 and 253 disposed on opposite sides of a lateral centerline Y—Y and opposed lateral edges 255 and 257 disposed on opposite sides of a longitudinal centerline X—X. Preferably, the lateral edges 255 and 257 of the wrapper 222 extend about 1.5" to 2.5", and even more preferably about 2.0", beyond the corresponding lateral edges 259 and 261 of the main absorbent body 228. As discussed above in conjunction with the first embodiment, this configuration not only facilitates securement of the napkin 220 to the wrapper 222, but also ensures that enough wrapper material is available to permit disposal of a used napkin 220 in the wrapper.

Referring again to FIG. 9, the sanitary napkin 220 includes an absorbent core 232 and an envelope 233 encasing the absorbent core 232. The envelope 233 includes a liquid-impervious backsheet or baffle 234 which is disposed below the absorbent core 232 and a liquid-permeable topsheet or cover 236 which is positioned above the absorbent core 232. The topsheet 236 is configured to face the user's body and functions to permit liquids to pass through it for retention by the absorbent core 232. The backsheet 234 has a back face 235 which is configured to be releasably secured to the first or article receiving surface 242 of the wrapper 222 by a garment adhesive 246 which could take the form a single strip as illustrated or which could be replaced by two or more discrete strips or patches. The topsheet 236 is secured to the backsheet 234 by a construction adhesive 238 located on an inner surface 239 of the topsheet 236 and a bodyside layer of construction adhesive 240 on the inner or front face 241 of the backsheet 238. As with the embodiment of FIGS. 1–7, this construction adhesive 240 could be eliminated in favor of a thermal bond if desired or by other bonding techniques known to those skilled in the art, such as ultrasonics.

As with the first embodiment, the assembly 224 is wrapped to form a package and may additionally be folded to form a pouch. Referring to FIG. 10, a package 225 is formed by folding the assembly 224 longitudinally about two longitudinally-extending fold lines 252 and 254, respectively, so that a side flap 256 and a side flap 258 extend laterally from the respective lateral edges 255 and 257 of the wrapper 222. The side flaps 256 and 258 rest on the topsheet 236 of the napkin 220 after folding as seen in the left half of FIG. 10. As discussed above in conjunction with the first embodiment, this wrapping protects the lateral edges 267 and 277 of the package 225 from contamination and obviates the need to seal the edges of the package 225, thereby facilitating production and also facilitating use, to the extent that there is no need to break a seal running the length of the package 225 when unwrapping the package 225. Preferably, the longitudinal fold lines 252 and 254 are coextensive with the longitudinal sides or edges 259 and 261 of the napkin 220 and are located such that the side flap 258 overlaps the other side flap 256 in the vicinity of the longitudinal centerline X—X of the package 225, thereby completely covering the napkin's topsheet 236. The side flaps 256 and 258 may be secured to one another by adhesive 260 in the form of one or more adhesive dots or strips (see FIG. 9) to facilitate subsequent folding and to provide a more compact package 225. Ends 269 and 271 of the package 225 also are preferably sealed to fully enclose the napkin as seen in conjunction with the end 269 of the left half of FIG. 10.

The package 225 preferably is folded longitudinally to produce an e-shaped pouch. This pouch is identical in appearance to the pouch 26 of the first embodiment and, accordingly, need not be discussed in detail.

The above-described individually wrapped sanitary napkins 20 or 220, as well as similarly configured absorbent articles, could be wrapped and folded by a variety of processes, including manually. It is preferred, however, that the wrapping and folding take place automatically on an in-line process that does not require interruption of assembly conveyance or sudden reversal in the direction of assembly conveyance. Exemplary processes for their practice now will be detailed in conjunction with the winged sanitary napkin 20 of the first embodiment, it being understood that the same or virtually the same process and apparatus could be used to wrap and fold the wingless sanitary napkin 220 of the second embodiment as well as other individually wrapped absorbent articles such as pantyliners, incontinent products, or the like.

Referring now to FIGS. 11 through 15, a first embodiment of a wrapper/folder system 100 is illustrated which forms assemblies 24 from sanitary napkins 20 and wrappers 22, wraps the assemblies 24 to form packages 25, and folds the packages 25 into pouches 26. All three operations are performed on an in-line process, without interrupting assembly conveyance and without reversing the direction of assembly conveyance. Referring first to FIG. 11, the system 100 includes as its principal components: an assembly former 102, a longitudinal folder 104, a seal and cut mechanism 106, and a two-stage folder 108. Components other than the two-stage folder 108 are identical or similar to the same or similar components used in similar processes known to those skilled in the art. These components therefore will be discussed only briefly and primarily by way of their function.

The assembly former 102 receives pre-formed napkins 20 and a continuous sheet of wrapper material 22' and applies the three garment adhesive strips 46, 48 and 50 to the continuous sheet of wrapper material 22' to form assemblies 24 connected end-to-end. The napkins 20 are then positioned on the continuous sheet of wrapper material 22' and the two members 22' and 20 are secured together by the garment adhesive 46, 48, and 50. In FIG. 11, the napkins 20 and continuous sheet of wrapper material 22' are fed into the assembly former 102 from above and below, respectively, by first and second conveyors 110 and 112. The first conveyor 110 can be a vacuum conveyor 110 having a downwardly-facing conveying surface. The second conveyor 112 can be a roller-driven belt conveyor disposed beneath the discharge end of the first conveyor 110 and having an upwardly-facing conveying surface. A standard adhesive applicator 114 applies the first, second and third garment adhesive strips 46, 48 and 50 to the continuous sheet of wrapper material 22' as the continuous sheet of wrapper material 22' is fed into the assembly former 102 by the second conveyor 112. Alternatively, the adhesive strips 46, 48 and 50 could be applied onto the napkins 20. The speeds of the conveyors 110 and 112 are coordinated in a known manner so that the first, second, and third garment adhesive strips 46, 48 and 50 register at the proper locations of a corresponding napkin 20. Assembly formation is completed by a conventional press roller 116 which presses the napkins 20 onto the continuous sheet of wrapper material 22' to set the pressure-sensitive garment adhesive strips 46, 48, and 50. It should be understood that the orientation of the assembly former 102 could be reversed so that the napkins 20 are fed into the assembly former 102 from below and so that the continuous sheet of wrapper material 22' is fed into the assembly former 102 from above. In this case, the vacuum conveyor 110 would be replaced by a conventional belt conveyor or the like.

Still referring to FIG. 11, the longitudinal folder assembly 104 folds the side flaps 56 and 58 of the continuous sheet of wrapper material 22' over the napkin topsheets 36. In the illustrated and preferred embodiment, the longitudinal folder assembly 104 includes an adhesive applicator 124 and a folding plow disposed over a discharge portion of the conveyor 112. The plow includes a pair of curved plow blades 126 and 128 that engage and fold the lateral opposed edges of the continuous sheet of wrapper material 22'. Specifically, as the continuous sheet of wrapper material 22' is conveyed to the left as viewed in the drawings, the plow blades 126 and 128 engage the side edges of the continuous sheet of wrapper material 22' forming the side flaps 56 and 58 and fold them longitudinally about the fold lines 52 and 54 in FIGS. 2 and 4 to create a package as described above. The plow blades 126 and 128 are staggered in the direction of sheet conveyance so that the two side flaps 56 and 58 are folded without interfering with one another, i.e., so that they are folded one on top of the other to form a seam in the vicinity of the longitudinal centerline X—X of the assemblies 24 (FIG. 3). The adhesive applicator 124 applies the above-described frangible adhesive strips 60 to the overlap or seam area of the first flap 56, and the second or opposing flap 58 is pressed by the second plow blade 128 into sealing contact with these adhesive strips 60. As noted above, these adhesive strips are not critical to assembly wrapping, and they could be replaced with tape or a thermal bond.

Three-dimensional vacuum conveyors could be used in combination with the plow blades 126 and 128. These conveyors would follow the contour of the plow blades 126 and 128 so that the side flaps 56 and 58 travel between the conveyors and the plow blades 126 and 128 under the guidance of the conveyors. Such conveyors would complicate the process, but would enhance process reliability and permit higher production rates. The use of three-dimensional vacuum conveyors in conjunction with folders is well-known to those skilled in the art, and a detailed description of conveyors suitable for this process therefore will be omitted for the sake of brevity.

Still referring to FIG. 11, the product leaving the longitudinal folder assembly 104 consists of a continuous string of packages 25 attached one to the other in an end-to-end fashion. The seal and cut assembly 106 then cuts the continuous sheet of wrapper material 22' between adjacent packages to form the individual packages 25, and seals the ends 69 and 71 of these packages 25 to fully-enclose the napkins 20 within the packages 25 like sausages. Seal and cut assemblies suitable for these purposes are well known to those skilled in the art. The typical such assembly includes a pair of spaced apart heated seal/cut rollers 136, 138. The lower roller 138 has a plurality of circumferentially spaced "anvils" each of which has an axially extending central glue applicator. As each anvil rotates in contact with the continuous sheet of wrapper material 22', the continuous sheet of wrapper material 22' is cut by the anvil, the applicator thermally bonds or otherwise seals the ends 69 and 71 of the now-separated and adjacent packages 25 while the anvil and mating roller 136 compress the sealed package ends 69 and 71. Individually wrapped and sealed packages 25 are formed at this time.

It should be noted that if the napkins 20 are fed into the wrapper/folder system 100 from below rather than from above, the downstream portion of the illustrated conveyor 112 would be replaced by a vacuum bed located above the packages 25, and the longitudinal folder assembly 104 would be placed beneath the vacuum box.

Still referring to FIG. 11, a flipper mechanism 140 is positioned downstream of the seal and cut assembly 106 for inverting the newly-formed packages 25 so that they are conveyed into the two-stage folder assembly 110 with their seams facing downwardly. The illustrated flipper mechanism 140 takes the form of a curved plate located immediately downstream of the seal and cut rollers 136 and 138. The packages 25 turn over as they slide over the concave surface of the plate and then are deposited in their inverted position on a downstream infeed conveyor 150 of the two-stage folder assembly 108. The flipper mechanism 140 could be replaced by twist belts of known construction or by any other suitable mechanism capable of turning the packages 25 180°. The flipper mechanism 140 also could be eliminated if the orientations of the conveyors 110 and 112 for the napkins 20 and continuous sheet of wrapper material 22' were to be inverted as described above or if the orientation of the two-stage folder assembly 108 were to be inverted as described below.

The two-stage folder assembly 108 tri-folds the packages 25 to form completed e-shaped pouches 26. Still referring to FIG. 11, the two-stage folded assembly 108 includes a first or infeed conveyor 150, first and second pusher assemblies 152 and 154, an adhesive applicator 156, and a second or outfeed conveyor 158.

The infeed conveyor 150 conveys the individually wrapped but not-yet folded packages 25 to the pusher assemblies 152 and 154 in a spaced-apart relationship. The speed of the conveyor 150 is controlled to match the speed of the pusher assemblies 152 and 154.

Still referring to FIG. 11, the pusher assemblies 152 and 154 reciprocate vertically and horizontally, respectively, to fold assemblies 24 into pouches 26. The pusher assemblies 152 and 154 may be reciprocated by cams, hydraulic cylinders, or the like. In the preferred embodiment, they are reciprocated by respective pneumatic cylinders 160 and 162. Each pusher assembly 152 or 154 has a flat pusher plate 164 or 166 attached to the rod end of the associated cylinder 160 or 162. Each pusher plate 164 or 166 should be at least as wide as the width of a package 25. A longitudinal slot 168, 170 is formed in the free end of each pusher plate 164, 166 for reasons which will become apparent below. The leading edge of each of the pusher plates 164 and 166 preferably is tapered or presents a radius so as to reduce the pressure imposed upon the packages 25 during pushing operations and to inhibit assembly cutting or slicing. The pusher plates 164, 166 also should be formed of a low friction material and/or treated with silicon or another friction reducing agent to facilitate assembly folding.

Guides are incorporated into the two-stage folder assembly 108 to direct movement of the packages 25 through the pusher assemblies 152 and 154 and to assist in the folding operation. These guides include first and second stationary guides 172 and 174 and first and second pivoting guides 176 and 178. The first stationary guide 172 comprises a curved plate which has a horizontal leg spaced above the discharge end of the infeed conveyor 150 and a vertical leg which extends upwardly from the discharge end of the infeed conveyor 150. The second stationary guide 174 comprises a C-shaped frame presenting a socket 182 (FIGS. 12–15) which faces the discharge end of the infeed conveyor 150 with a short gap therebetween of sufficient thickness to receive the pusher blade 164. The socket 182 receives the leading edges of conveyed packages to prevent them from overshooting the pusher assembly 152. The first pivoting guide 176 comprises a curved plate 184 which is spaced from the first stationary guide 172 to present an assembly-receiving gap therebetween. The plate 184 curves upwardly and to the left in the drawings and is pivotable with a pivot pin 186 from a generally vertical orientation (FIGS. 11 and 12) to an orientation in which its upper end is positioned adjacent the entrance of the outfeed conveyor 158 (FIG. 15). The second pivoting guide 178 comprises a C-shaped frame 188 which presents a socket 190 (FIGS. 12–13 and 15) and which is pivotable with a pivot pin 192 from a generally vertical orientation (FIGS. 11 and 12) to an orientation in which its lower end is positioned adjacent the entrance of the outfeed conveyor 158 (FIG. 15).

As best seen in FIG. 14, the adhesive applicator 156 is mounted on a laterally central portion of the vertical leg of the first stationary guide 172 so as to be capable of injecting adhesive through an orifice 180 in the guide 172, through the slot 168 of the pusher plate 164, and onto a package 25 being driven by the pusher plate 164. This applicator 156 could, however, be replaced by a tape applicator or some other suitable structure.

Referring again to FIG. 11, the outfeed conveyor 158 is formed from a pair of spaced-apart continuous belt conveyors 200 and 202. The conveyors 200 and 202 convey pouches 26 away from the pusher assemblies 152 and 154 while compressing the pouches 26 in a nip 204 formed between the conveyors 200 and 202 to reduce their overall thickness and to press the adhered flaps 68 and 70 of each pouch 26 into sealing engagement at the locations of the adhesive patch 72. The lower conveyor 202 includes an upwardly-inclined entrance section 206 which receives pouches 26 from the pusher assembly 154 and which feeds the pouches 26 into the nip 204.

Figure 12:
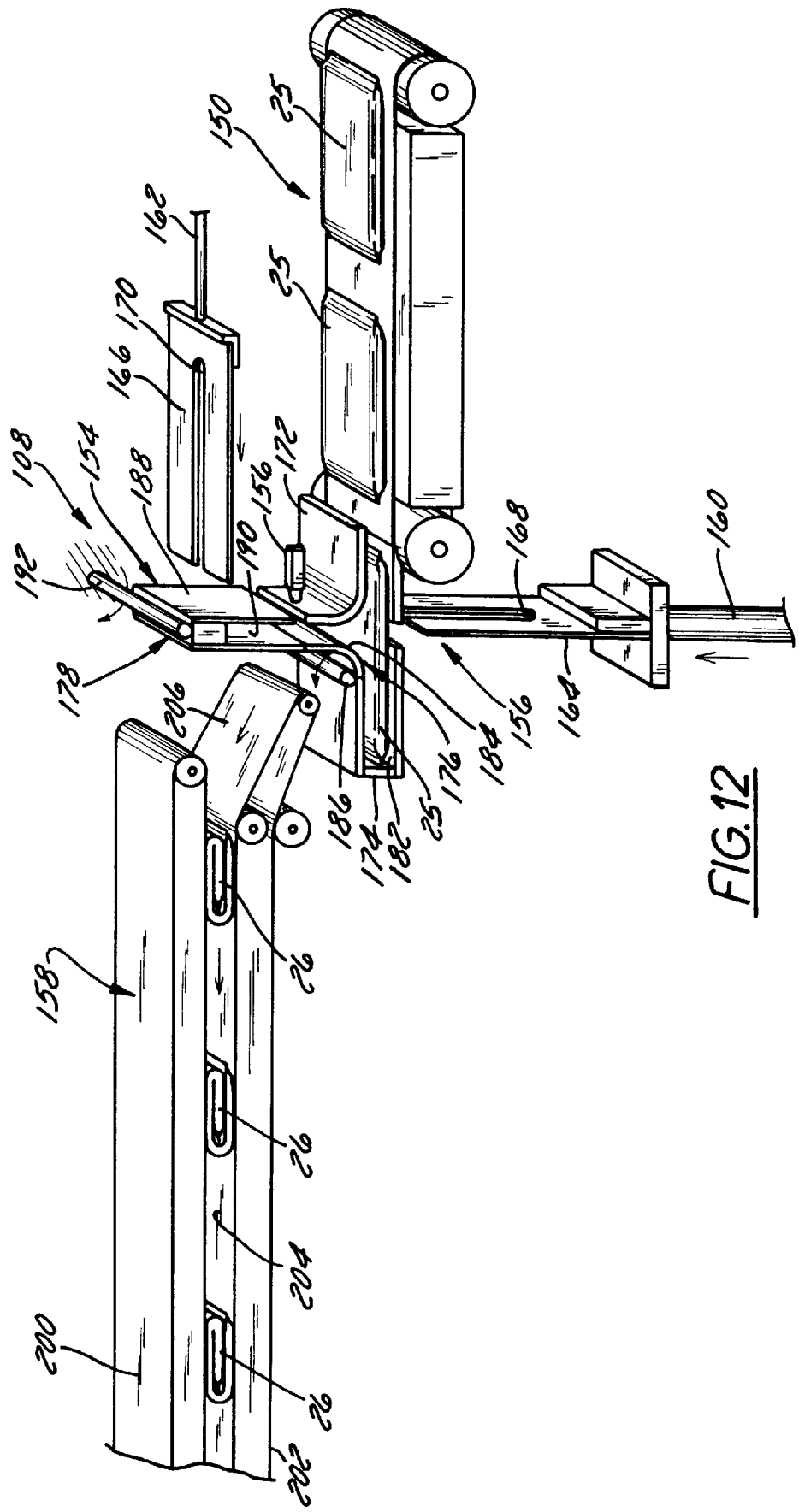
FIG. 12 is a partially schematic perspective view illustrating a two-stage folder assembly of the system depicted in FIG. 11 and illustrates a first stage of its sequence of operation in which a package is positioned for folding into a pouch by the two-stage folder assembly.

Pouches 26 are formed in the two-stage folder assembly 108 as follows:

Referring to FIG. 12, packages 25 are fed into the two-stage folder assembly 108 from the infeed conveyor 150 with the longitudinal seams (formed by the overlapping portions of the side flaps 56 and 58) facing downwardly. As a package enters the two-stage folder assembly 108, the pusher plate 164 of the first pusher assembly 152 is driven upwardly by its pneumatic cylinder 160 so as to engage the package 25 near the lateral fold line 62. Continued upward movement of the pusher plate 164 lifts the package 25 from the plane of the infeed conveyor 150 so that the package 25 is forced between the curved guides 172 and 176 as illustrated in FIG. 13, thereby partially folding the first longitudinal flap 68 over the central portion 66. The adhesive applicator 156 is activated at this time as illustrated in FIG. 14 to spray a patch 72 of adhesive (FIGS. 4 and 5) through the slot 168 of the first pusher plate 164 and onto the end of the second longitudinal flap 70. Continued upward movement of the first pusher plate 164 forces a portion of the package 25 comprising the junction of the central portion 66 and the first longitudinal flap 68 into the socket 190 of the second pivoting guide 178 as illustrated in FIGS. 13 and 14. Movement of the partially-folded, now U-shaped package 25 into the socket 190 further folds the first longitudinal flap 68 over the central portion 66 and the first pusher plate 164.

Next, movement of the first pusher assembly 152 is reversed to retract the first pusher plate 164 form the socket 190, and the second pusher assembly 154 is extended to drive the second pusher plate 166 towards the second pivoting guide 178. Metal-to-metal contact between the pusher plate 166 and the guide 178 could be eliminated by mechanically coupling the pivot pin 192 to the pusher assembly 154 by a pivot linkage, cam, or the like (not shown). The guide 178 then would pivot without being contacted by the pusher plate 166.

As the pusher plate 166 continues to extend, it moves along the guide 178 and into contact with the package 25 at a location adjacent the lateral fold line 64 between the central portion 66 and the second flap 70 as seen in FIG. 15. Continued movement of the pusher plate 166 pushes the package 25 out of the socket 190 and towards the outfeed conveyor 158. During this motion, the second longitudinal flap 70 of the package 25 engages the first pivoting guide 176 and begins to fold over the first longitudinal flap 68 (thereby forming a pouch 26) while it forces the guide 176 to pivot to the position illustrated in FIG. 15. The slot 170 in the second pusher plate 166 is aligned with the adhesive patch 72 on the second flap 70 at this time so that the pusher plate 166 does not smear the adhesive patch 72. Additional pusher plate movement forces the pouch 26 onto the upwardly-inclined entrance section 206 of the lower belt 202 of the discharge conveyor 158 to cause the second longitudinal flap 70 of the pouch 26 to bend further over the first longitudinal flap 68. The outfeed conveyor 158 then conveys the pouch 26 away from the second pusher assembly 154 and into the nip zone 204 where the pouch 26 is compressed to compact it and to set the pressure sensitive adhesive patch 72. The outfeed conveyor 158 then conveys the finished pouch 26 out of the system 100 for subsequent action such as packaging in cartons or boxes.

Referring now to FIGS. 16 through 24, a wrapper/folder system 300 is illustrated which is constructed in accordance with another embodiment of the invention and which forms assemblies 24 from sanitary napkins 20 and wrappers 22, wraps the assemblies 24 to form packages 25, and laterally tri-folds the packages 25 into e-shaped pouches 26. As in the embodiment of FIGS. 11–15, all three operations are performed in an in-line process, without interrupting assembly conveyance and without reversing the direction of assembly conveyance.

Figure 16:
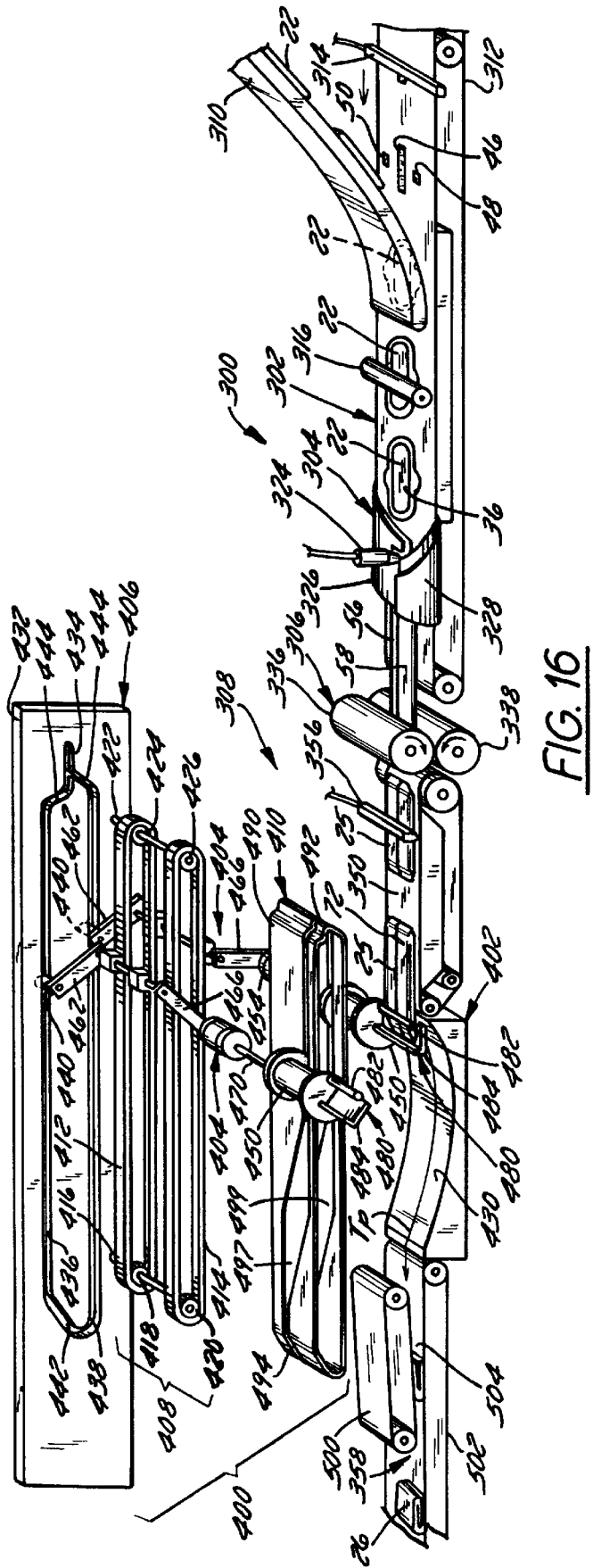
FIG. 16 is a partially schematic perspective view of a second wrapper/folder system for combining an absorbent article and wrapper to form an assembly, folding the assembly into a package, and then forming the package into a pouch.

Referring first to FIG. 16, the wrapper/folder system 300 includes as its principal components: an assembly former 302, a longitudinal folder 304, a seal and cut mechanism 306, and a tri-folder system 308. Components other than the tri-folder system 308 are identical or similar to the same or similar components of the embodiment of FIGS. 11-15 and will be discussed only briefly and primarily by way of their function.

Still referring to FIG. 16, The assembly former 302 receives pre-formed napkins 20 and a continuous sheet of wrapper material 22' and applies garment adhesive strips to the continuous sheet of wrapper material 22' to form assemblies 24 connected end-to-end. The napkins 20 are then positioned on the continuous sheet of wrapper material 22', and the two members 22' and 20 are secured together by the garment adhesive 46, 48, and 50. The napkins 20 and continuous sheet of wrapper material 22' are fed into the assembly former 302 from above and below, respectively, by first and second conveyors 310 and 312. The first conveyor 310 can be a vacuum conveyor 310 having a downwardly-facing conveying surface. The second conveyor 312 can be a roller-driven belt conveyor disposed beneath the discharge end of the first conveyor 310 and having an upwardly-facing conveying surface. A standard adhesive applicator 314 applies the first, second and third garment adhesive strips 46, 48 and 50 to the continuous sheet of wrapper material 22' as the continuous sheet of wrapper material 22' is fed into the assembly former 302 by the second conveyor 312. Alternatively, the adhesive strips 46, 48 and 50 could be applied onto the napkins 20. The speeds of the conveyors 310 and 312 are coordinated in a known manner so that the first, second, and third garment adhesive strips 46, 48 and 50 register at the proper locations of a corresponding napkin 20. Assembly formation is completed by a conventional press roller 316 which presses the napkins 20 onto the continuous sheet of wrapper material 22' to set the pressure-sensitive garment adhesive strips 46, 48, and 50. As discussed above in conjunction with the embodiment of FIGS. 11–15, the orientation of the assembly former 302 could be reversed so that the napkins 20 are fed into the assembly former 302 from below and so that the continuous sheet of wrapper material 22' is fed into the assembly former 302 from above. In this case, the vacuum conveyor 310 would be replaced by a conventional belt conveyor or the like.

Still referring to FIG. 16, the longitudinal folder assembly 304 folds the side flaps 56 and 58 of the continuous sheet of wrapper material 22' over the napkin topsheets 36. The longitudinal folder assembly 304 includes an adhesive applicator 324 and a folding plow disposed over a discharge portion of the conveyor 312. The plow includes a pair of curved plow blades 326 and 328 that engage and fold the lateral opposed edges of the continuous sheet of wrapper material 22'. Specifically, as the continuous sheet of wrapper material 22' is conveyed to the left as viewed in the drawings, the plow blades 326 and 328 engage the side edges of the continuous sheet of wrapper material 22' forming the side flaps 56 and 58 and fold them longitudinally about the fold lines 52 and 54 in FIGS. 2 and 4 to create a package 25 as described above. The plow blades 326 and 328 are staggered in the direction of sheet conveyance so that the two side flaps 56 and 58 are folded without interfering with one another, i.e., so that they are folded one on top of the other to form a seam in the vicinity of the longitudinal centerline X—X of the assemblies 24 (FIG. 3). The adhesive applicator 324 applies the above-described frangible adhesive strips 60 to the overlap or seam area of the first flap 56, and the second or opposing flap 58 is pressed by the second plow blade 328 into sealing contact with these adhesive strips 60. Three-dimensional vacuum conveyors could be used in combination with the plow blades 326 and 328. These conveyors would follow the contour of the plow blades 326 and 128 so that the side flaps 56 and 58 travel between the conveyors and the plow blades 326 and 328 under the guidance of the conveyors. Such conveyors would complicate the process, but would enhance process reliability and permit higher production rates.

Still referring to FIG. 16, the product leaving the longitudinal folder assembly 304 consists of a continuous string of packages 25 attached one to the other in an end-to-end fashion. The seal and cut assembly 306 then cuts the continuous sheet of wrapper material 22' between adjacent packages to form the individual packages 25, and seals the ends 69 and 71 of these packages 25 to fully-enclose the napkins 20 within the packages 25 like sausages. The seal and cut assembly 304 includes a pair of spaced apart, upper and lower heated seal/cut rollers 336, 338. The lower roller 338 has a plurality of circumferentially spaced "anvils" each of which has an axially extending central glue applicator. As each anvil rotates in contact with the continuous sheet of wrapper material 22', the continuous sheet of wrapper material 22' is cut by the anvil, the applicator thermally bonds or otherwise seals the ends 69 and 71 of the now-separated and adjacent packages 25 while the anvil and mating roller 336 compress the sealed package ends 69 and 71. Individually wrapped and sealed packages 25 are formed at this time.

As with the embodiment of FIGS. 11–15, if the napkins 20 are fed into the system 300 from below rather than from above, the downstream portion of the illustrated conveyor 312 would be replaced by a vacuum bed located above the packages 25, and the longitudinal folder assembly 304 would be placed beneath the vacuum box.

The tri-folding system 308 tri-folds the packages 25 to form completed e-shaped pouches 26. Still referring to FIG. 16, the tri-folding system 308 includes a first or infeed conveyor 350, an in-line tri-folder assembly 400, and a second or outfeed conveyor 358.

Still referring to FIG. 16, the infeed conveyor 350 and outfeed conveyor 358 convey individually wrapped but not-yet folded packages 25 to the in-line tri-folder assembly 400 and convey folded pouches 26 from the in-line tri-folder, respectively. The speeds of the conveyors 350 and 358 are controlled to match the speed of the in-line tri-folder assembly 400. An applicator 356 is disposed over the infeed conveyor 350 so as to be capable of injecting a strip or patch 72 of adhesive onto each package for subsequent bonding of the first and second longitudinal flaps 68 and 70 to one another. The outfeed conveyor 358 is formed from a pair of spaced-apart continuous belt conveyors 500 and 502. The belt conveyors 500 and 502 convey pouches 26 away from the in-line tri-folder assembly 400 while compressing the pouches 26 in a nip 504 formed therebetween to reduce the thickness of each pouch and to press the adhered longitudinal flaps 68 and 70 of each pouch 26 into sealing engagement at the location of the adhesive patch 72.

Still referring to FIG. 16, the in-line tri-folder assembly 400 is designed to fold the wrapped packages 25 into e-shaped pouches 26 as the packages 25 travel through the in-line tri-folder assembly 400 and without terminating package conveyance or reversing the direction of package travel. The in-line tri-folder assembly 400 includes a support structure 402 that defines a travel path $T_P$ for the conveyance of packages through the in-line tri-folder assembly 400 and additionally includes a plurality of tri-folding mechanisms 404. The tri-folding mechanisms 404 are collectively supported by a common support track 406, translated at least generally in parallel with the travel path $T_P$ by an endless drive element 408, and guided in their movement generally along the travel path $T_P$ by a guide track 410. Each of the tri-folding mechanisms 404 rotates as it is driven generally along the travel path $T_P$ by the endless drive element 408 so as to fold a respective package 25 into an e-shaped pouch 26.

Figure 17:
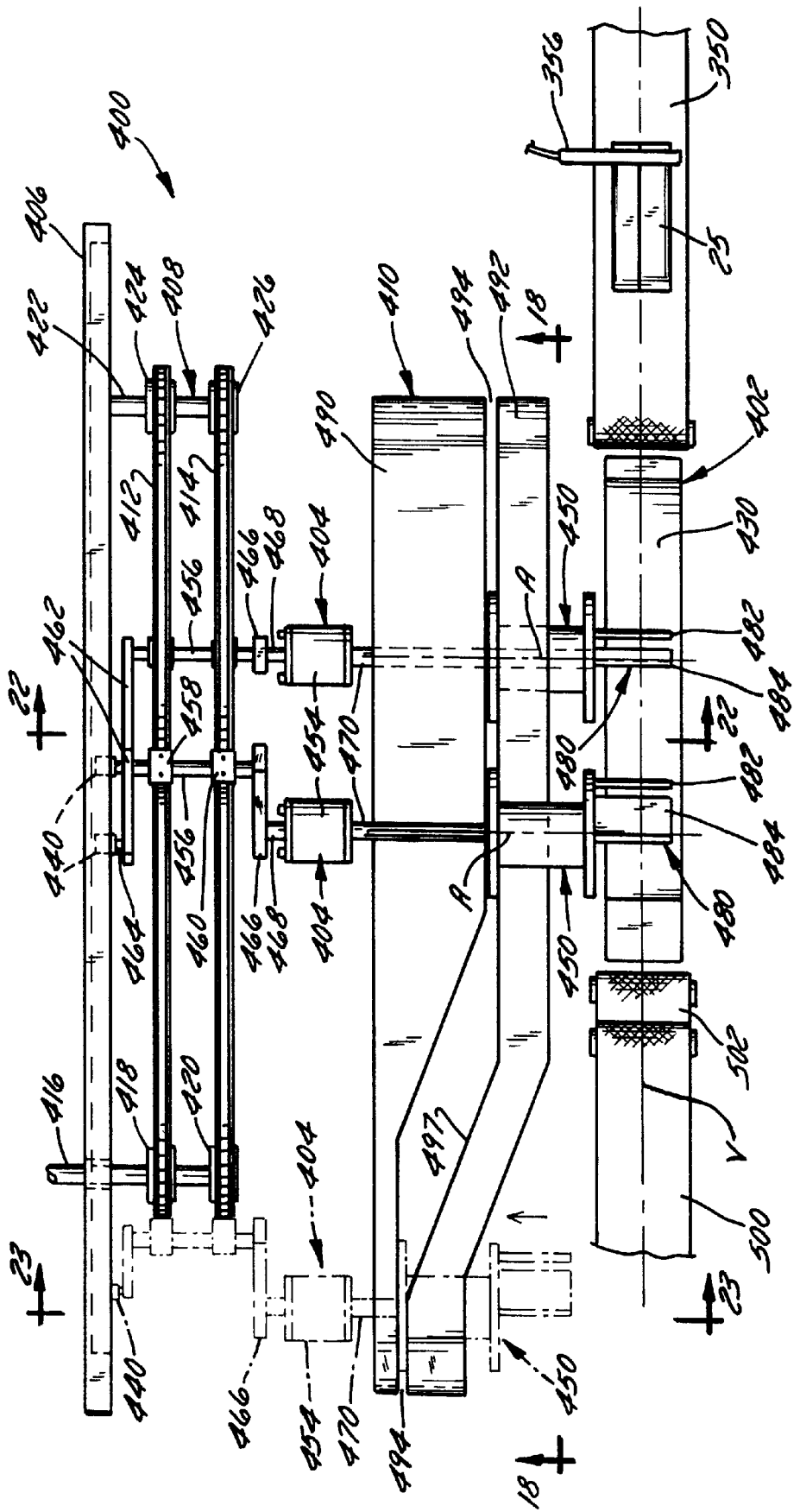
FIG. 17 is a top plan view of a tri-folding system of the wrapper/folder system of FIG. 16 and illustrates the conveyance of a package to be folded towards the tri-folding system.

Referring to FIG. 17, the travel path $T_P$ extends in a vertical plane V, and each of the tri-folding mechanisms 404 extends at least generally transversely with respect to the plane V. The support track 406, endless drive element 408, and guide track 410 all extend at least generally in parallel with the vertical plane V and transversely with respect to rotational axes A of spindles 450 of the tri-folding mechanisms 404. The guide track 410 is positioned between the vertical plane V and the endless drive element 408, and the endless drive element 408 is positioned between the guide track 410 and the support track 406. At least two tri-folding mechanisms 404 are spaced longitudinally along the endless drive element 408 so that more than one package 25 can be folded in each revolution of the endless drive element 408.

Still referring to FIG. 17, the endless drive element 408 may comprise any structure capable of conveying the individual tri-folding mechanisms 404 around the in-line tri-folder assembly 400 in a continuous loop. In the illustrated embodiment, the endless drive element 408 comprises a pair of spaced-apart endless chains 412 and 414. The chains 412 and 414 are driven at one end by a common drive shaft 416 and respective drive sprockets 418 and 420 and supported at another end by an idler shaft 422 and respective idler sprockets 424 and 426.

Figure 18:
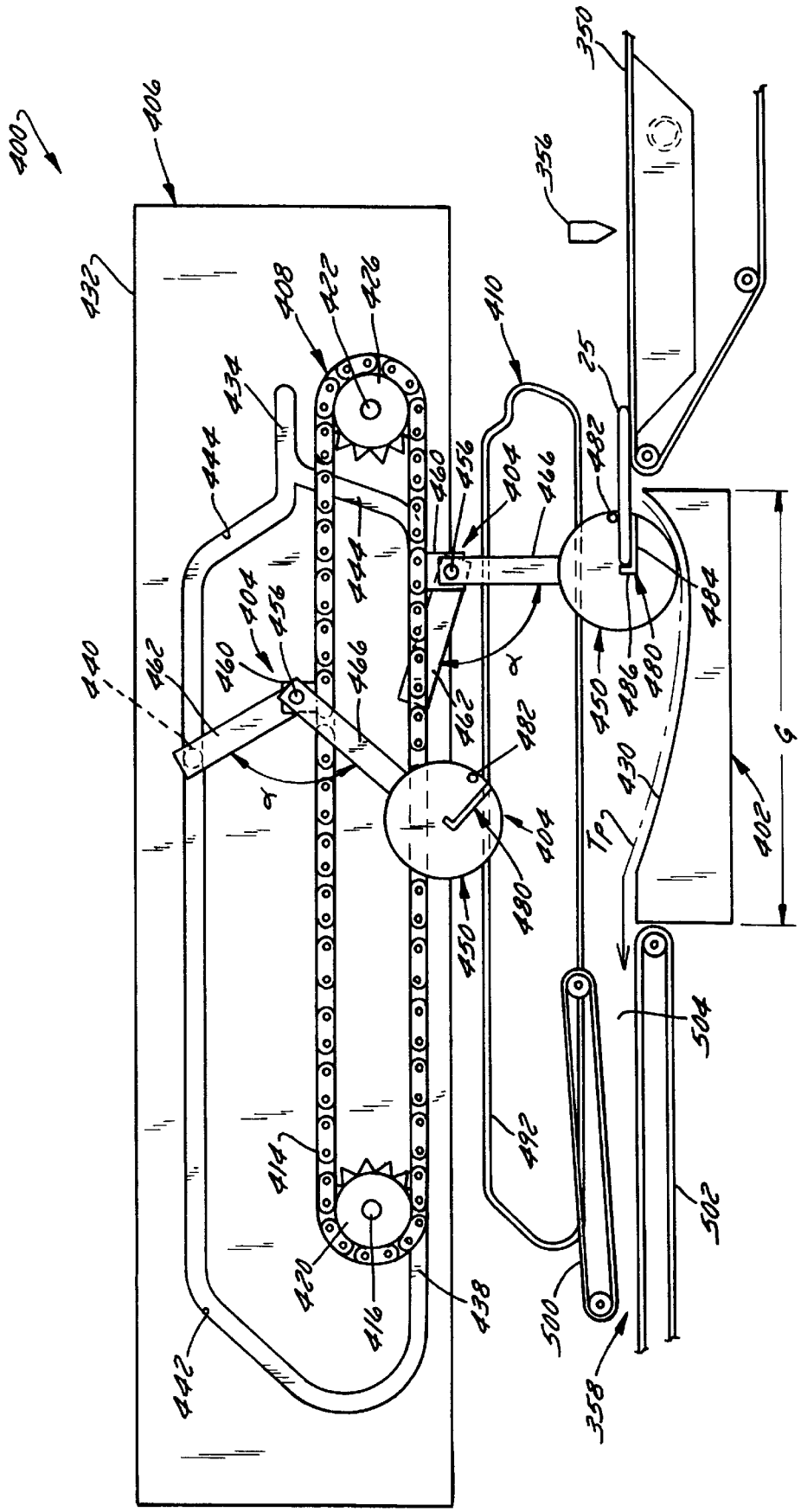
FIG. 18 is a side sectional elevation view taken along the lines 18—18 in FIG. 17 and illustrates the receipt of a package to be folded by a tri-folding mechanism of the tri-folding system of FIG. 17.

Referring to FIG. 18, the package support structure 402 spans a longitudinal gap G between the infeed conveyor 350 and the discharge conveyor 358 so as to support the packages 25 as they are being conveyed and folded by the tri-folding mechanisms 404. The support structure 402 includes an upper curved surface 430 along which the packages 25 slide and which is preferably coated with a friction-reducing substance such as a plasma coating. This surface is curved within the vertical plane V so as to accommodate rotation of the operative components of the tri-folding mechanisms 404 during package folding. The curvature of the surface 430 will depend in part on the desired location of the lateral fold lines 62 and 64 (FIGS. 4 and 5) along the longitudinal length of the package 25. The more pronounced the curvature, the shorter the central longitudinal portion 66 of the folded pouch 26 and the longer the first and second longitudinal flaps 68 and 70. The profile of the illustrated surface 430, when employed in conjunction with the illustrated tri-folding mechanisms 404 (best seen in FIG. 19), will result in the formation of a pouch in which each longitudinal flap 68 and 70 has a length which is about 25–30% of the longitudinal length of the package 25.

Still referring to FIG. 18, the support track 406 may comprise any structure capable of supporting the tri-folding mechanisms 404 and of effecting an elevation change of the tri-folding mechanisms 404 as they revolve around the in-line tri-folder assembly 400 with the endless drive element 408. In the illustrated embodiment, the support track 406 comprises a metal plate 432 having a slot or channel 434 formed therein which is segmented into upper and lower portions 436 and 438 and in which rides support rollers 440 of the tri-folding mechanisms 404. The roller 440 of each tri-folding mechanism 404 rides in the lower slot portion 438 during a package folding operation and then, upon reversal of tri-folding mechanism directional movement, moves up an inclined portion 442 of the slot 434 to lift the tri-folding mechanism 404 above the travel path $T_P$. The tri-folding mechanism 404 then returns in the upper slot portion 438 and then moves through a generally sideways Y-shaped portion 444 of the slot 434 that connects the upper and lower portions 436 and 438 so as to lower the tri-folding mechanism 404 into the travel path $T_P$ for receiving another package 25 to be tri-folded.

Figure 19:
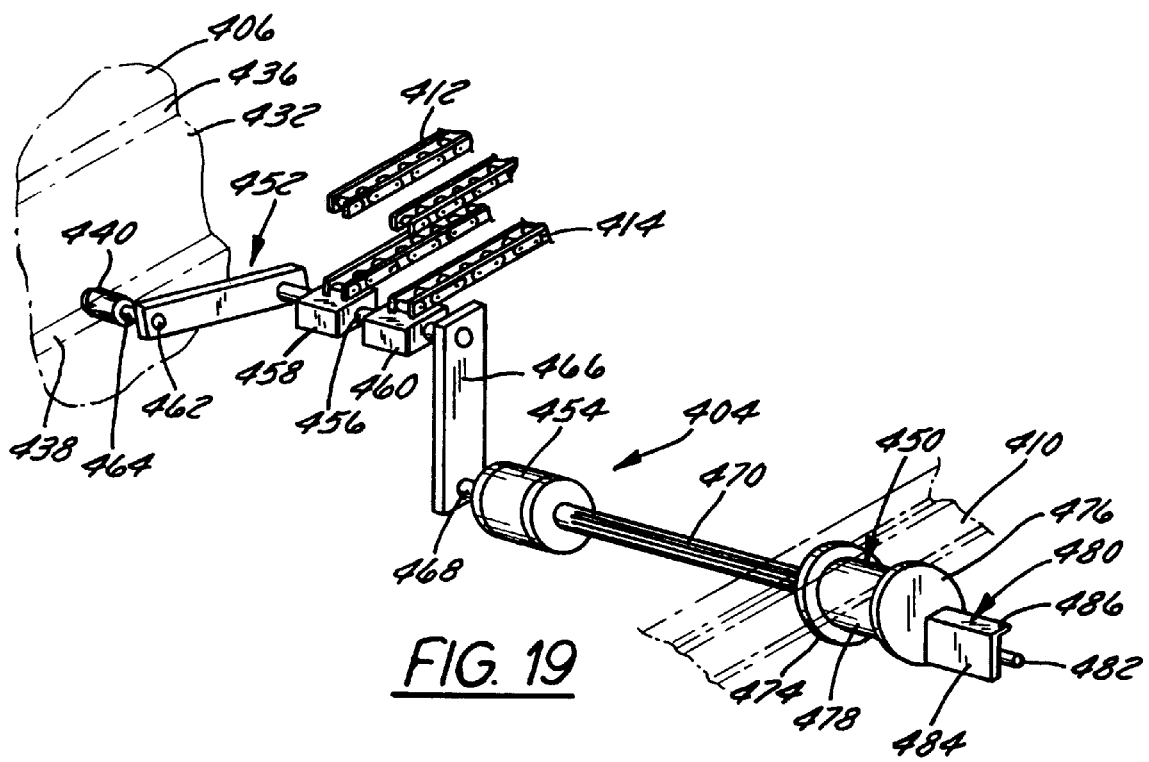
FIG. 19 is a perspective view of a tri-folding mechanism of the tri-folding system of FIGS. 16–18 and of cooperating components of the remainder of the tri-folding system.

Referring particularly to FIG. 19, each tri-folding mechanism 404 comprises: a spindle 450 on which is mounted the operative components of the tri-folding mechanism 404; a linkage assembly 452 which supports and drives the spindle 450; and a motor 454 which is supported on the linkage assembly 452 and which drives the spindle 450 to rotate while permitting movement of the spindle 450 transversely with respect to the linkage assembly 452. The linkage assembly 452 includes a horizontal support pin 456 that extends through blocks 458 and 460 which in turn are fixed to the drive chains 412 and 414. One end of the support pin 456 is coupled to the above-mentioned support roller 440 by a first arm 462 having an upper end pivotally connected to a support shaft 464 for the support roller 440 and a lower end pivotally connected to the support pin 456. Another end of the support pin 456 supports the motor 454 via a second arm 466 having an upper end pivotally connected to the pin 456 and a lower end on which is affixed a support rod 468 for the motor 454. Due to the configuration of the support track 406 and guide track 410, the angle a (FIG. 18) between the arms 462 and 466 remains constant as the tri-folding mechanism 404 revolves around the in-line tri-folder assembly 400 with the endless drive element 408.

Figure 20:
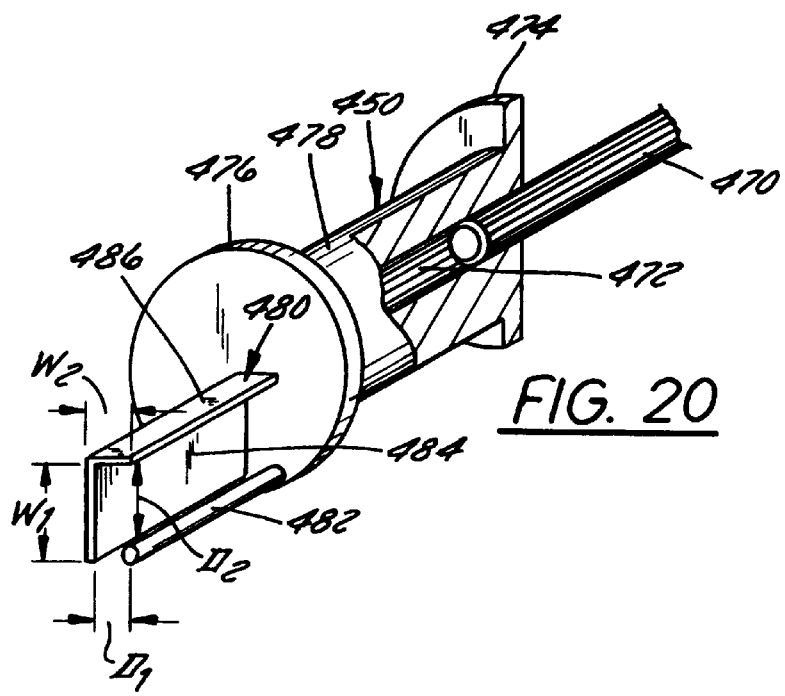
FIG. 20 is a perspective view of a spool of the tri-folding mechanism of FIG. 19 and of a cooperating portion of a splined support shaft for the spool.

The motor 454 may comprise any suitable variable speed motor and preferably comprises an AC servo-positioning motor. Motor 454 has a rotatable output shaft 470 which is splined so as to mate with a splined axial bore 472 in the spindle 450 as seen in FIG. 20. This splined connection permits relative axial motion between the spindle 450 and the motor output shaft 470 while prohibiting relative rotational motion between the spindle 450 and the output shaft 470. This arrangement therefore permits the above-described transverse movement of the spindle 450 relative to the motor 454 and the vertical plane V.

Still referring to FIG. 20, the spindle 450 includes an axially-inner guide disk 474 and an axially-outer support disk 476 separated from one another by a body 478 which is of reduced diameter when compared to the disks 474 and 476. The guide disk 474 is captured and guided by the guide track 410 as detailed below. The support disk 476 supports operative components of the spindle 450. In the illustrated embodiment, these operative components include an L-shaped folding plate 480 and a cylindrical folding pin 482. The folding plate 480 has a first, relatively wide leg 484 and a second, relatively narrow leg 486 extending at right angles from one another. The wide leg 484 forms a support surface for the first longitudinal flap 68 of the package 25 to be folded. The narrow leg 486 forms a stop for the end 69 of the first longitudinal flap 68 of the package 25. The width $W_1$ of the wide leg 484 should be slightly less than the intended length of the first longitudinal flap 68 and preferably should extend about 20–30% of the length of the package 25. In the illustrated embodiment in which the package 25 has a length of about 9½", the width $W_1$ should be between about 2" and 2¾" and most preferably about 2½". The width $W_2$ of the short leg 486 should be no greater than the thickness of the package 25. In the illustrated embodiment in which the package 25 has a thickness of approximately ⅜", the width $W_2$ should be no greater than ⅜" and preferably should be about 5/16". The folding plate 480 and folding pin 482 should each have a length L that is at least as long as the width of the package 25, namely, at least 3½" in the illustrated embodiment. In order to facilitate movement of the packages 25 relative to the tri-folding mechanism 404 at the appropriate times, the folding pin 482 and the folding plate 480 preferably are coated with a non-stick substance such as a plasma coating.

Still referring to FIG. 20, the folding pin 482 is spaced from the wide and narrow legs 484 and 486 of the folding plate 480 by distances $D_1$ and $D_2$ respectively. The distance $D_1$ between the folding pin 482 and the wide leg 484 should be sufficiently long to provide clearance for the package 25 but not so long as to permit excessive radial movement of the package 25 relative to the spindle 450. In the illustrated embodiment in which the package 25 is approximately ⅜" thick, this spacing should be approximately ½". The distance $D_2$ between the folding pin 482 and the narrow leg 486 should approximately equal the width $W_1$ of the wide leg 484.

Figure 21:
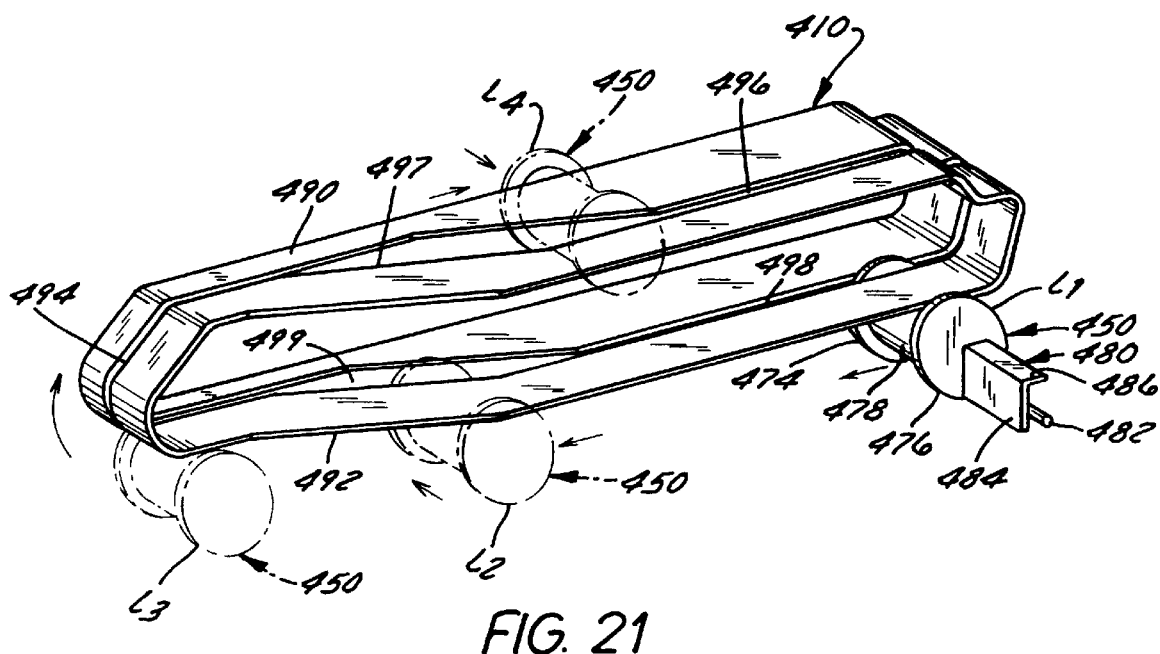
FIG. 21 is a perspective view of a guide track of the tri-folding system of FIGS. 16–18 and illustrates movement of the spool of one of the tri-folding mechanisms around the guide track.
Figure 22:
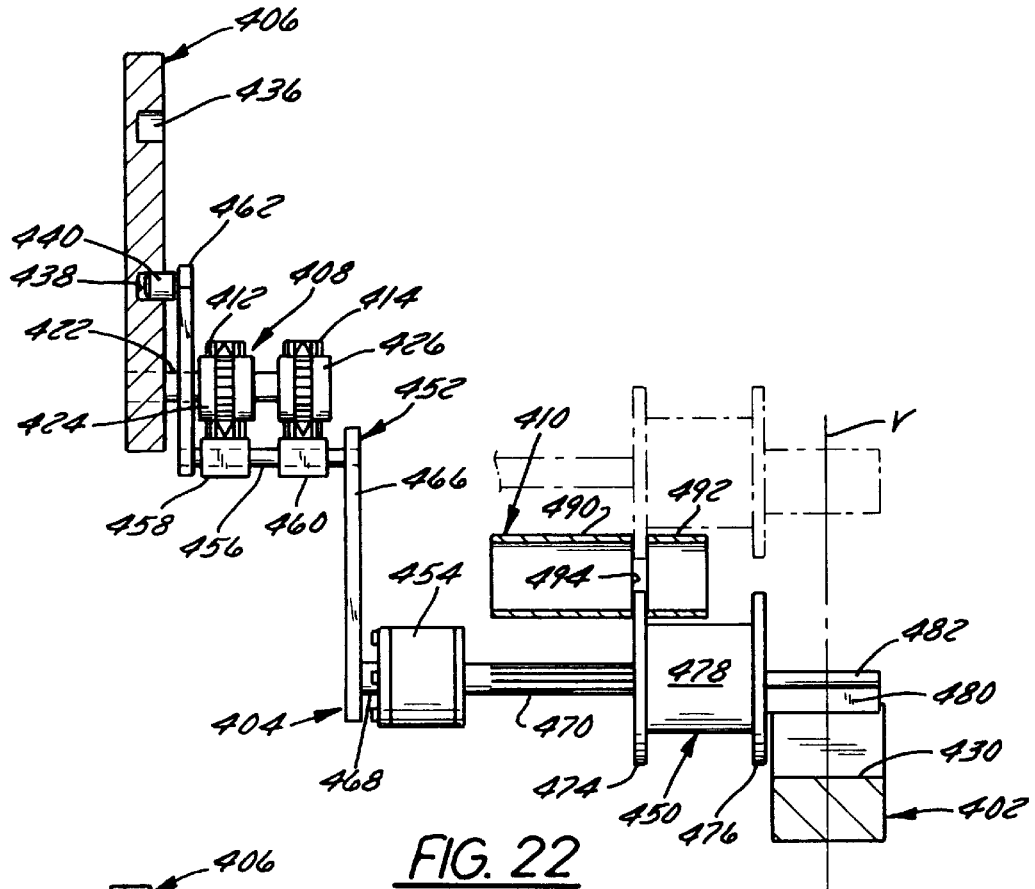
FIG. 22 is a sectional end view taken generally along the lines 22—22 in FIG. 17 and illustrates one of the tri-folding mechanisms of the tri-folding system in a position in which the tri-folding mechanism is capable of folding a package into a pouch.
Figure 23:
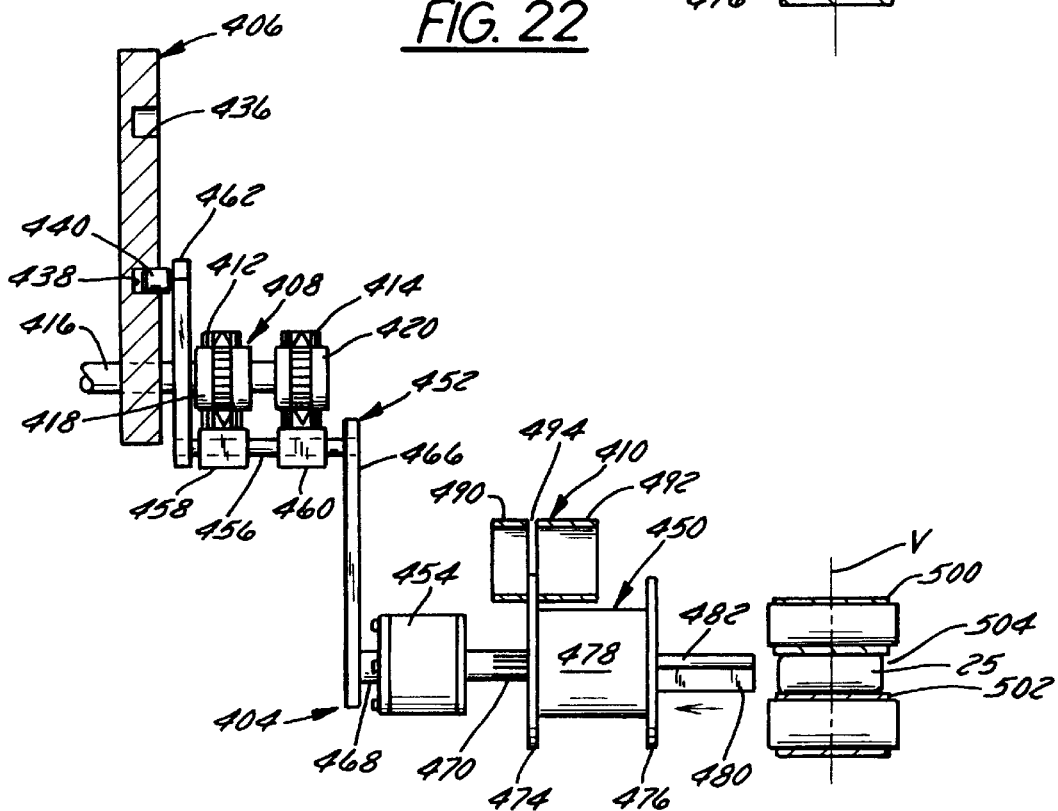
FIG. 23 is a sectional end view taken generally along the lines 23—23 in FIG. 17 and illustrates the spool of one of the tri-folding mechanisms of the tri-folding system in a position in which it is capable of movement through the tri-folding system without interfering with the transfer of other packages through the tri-folding system.

The primary purpose of the guide track 410 is to cause the spindle 450 of each tri-folding mechanism 404 to move towards and away from the vertical plane V as the spindle 450 revolves around the in-line tri-folder assembly 400 with the endless drive element 408 so that the folding plate 480 and folding pin 482 of the tri-folding mechanism 404 may move into and out of the travel path $T_P$. This function could be performed by a powered reciprocating element such as a pneumatic cylinder, a hydraulic cylinder, or an electric screw actuator that is located in series with the endless drive element 408, the motor 454, and the spindle 450. This finction could also be performed by any of a variety of cam mechanisms. In the preferred embodiment, this function is enabled by configuring the guide track 410 to act as a cam follower so as to control the lateral or transverse position of the spindle 450 relative to the vertical plane V and hence to the travel path $T_P$. Referring to FIG. 21, guide track 410 comprises two transversely-spaced generally ovoid plates 490, 492 extending at least generally in parallel with the vertical plane V (as seen in FIG. 17). A generally ovoid slot 494 is defined by facing edges of the plates 490 and 492 and is divided into upper and lower portions 496, 498. The guide disk 474 of the spindle 450 of each of the tri-folding mechanisms 404 is captured in this slot 494 so that opposite axial faces of the guide disk 474 engage at least one and preferably both of the facing edges of the slot 494. The profile of the slot 494 essentially matches the profile of the slot or channel 434 in the support track 406 so that the support roller 440 and guide disk 474 of each tri-folding mechanism 404 follow essentially the same path. The upper and lower portions 496 and 498 of the slot 494 each additionally include an inclined section 497 and 499 that extends at an acute horizontal angle with respect to the vertical plane V so as to effect the above-described transverse or lateral movement of the spindle 450 relative to the motor 454 and vertical plane V as the spindle 450 travels along the slot 494. Hence, when a spindle 450 is located upstream of the section 499 as illustrated at the location $L_1$ in solid lines in FIG. 21, engagement between the guide disk 474 and the edges of the slot 494 hold the spindle 450 at a position which is spaced from the motor 454 and adjacent the vertical plane V as seen in FIG. 22. Conversely, after the spindle 450 traverses the inclined section 499 of the slot portion 498 as illustrated at the location $L_2$ in FIG. 21 and travels to the location $L_3$, the spindle 450 is driven towards the motor 454 and away from the vertical plane V as illustrated in FIG. 23 so that the folding plate 480 and folding pin 482 are spaced transversely from the vertical plane V. Continued movement of the spindle 450 around the in-line tri-folder assembly 400 results in guidance of the guide disk 474 through the inclined section 497 of the upper slot portion 496 and to the location $L_4$ to return the spindle 450 to a position adjacent the vertical plane V.

Pouches 26 are formed in the tri-folding system 308 as follows:

Referring to FIG. 16, packages 25 are fed into the tri-folding system 308 from the infeed conveyor 350 with their longitudinal seams (formed by the overlapping portions of the side flaps 56 and 58) facing upwardly. As a package 25 enters the tri-folding system 308, the adhesive applicator 356 applies a patch or strip 72 of adhesive to the package 25. This patch 72 is located so as to avoid contact with the folding plate 480 during the folding operation. As with the pusher plates of the first embodiment, the folding plate 280 may, if necessary, be slotted to accommodate the adhesive strip or patch 72. Also, as in the first embodiment, the strip 72 could be replaced by a strip of tape or the like.

The package 25 is then conveyed from the end of the infeed conveyor 350 and into the in-line tri-folder assembly 400. At this time, one of the tri-folding mechanisms 404 has been driven by the endless drive element 408 to the position illustrated in FIG. 16 in which the folding plate 480 is disposed adjacent the discharge end of the infeed conveyor 350 and in which the motor 454 has driven the spindle 450 to rotate about its axis A to a position in which the wide leg 484 of the folding plate 480 is disposed horizontally and located essentially coplanar with the support surface of the infeed conveyor 350. The package 25 is then conveyed between the folding plate 480 and the folding pin 482 so that it is supported on the wide leg 484 of the folding plate 480 and so that its end 69 abuts the narrow leg 486 of the folding plate 460.

The tri-folding mechanism 404 then folds the package 25 into a pouch 26 by rotating through a full 3600 revolution as it traverses the length of the in-line tri-folder assembly 400. Specifically, referring to FIG. 24, simultaneous rotational movement and longitudinal translation of the spindle 450 from its initial package-receiving position of FIG. 16 to the position P, (FIG. 24) causes the folding plate 480 to rotate above the folding pin 482 to begin to bend the first longitudinal flap 68 of the package 25 about the central portion 66. This initial folding captures the package so that the package 25 is conveyed through the in-line tri-folder assembly 400 upon continued spindle translation under power of the endless drive element 408. The spindle 450 continues to rotate and translate through the positions $P_2$, $P_3$, and $P_4$ in FIG. 24 until the spindle 450 has rotated approximately 270° from its initial position. At this time, the first longitudinal flap 68 of the package 25 is fully-folded about the folding pin 482 and is aligned adjacent to the central portion 66 of the package 25. The guide disk 474 of the spindle 450 enters the inclined section 499 of the lower portion 498 of the slot 494 in the guide track 410 at about this time so as to begin to withdraw the folding plate 480 and folding pin 482 transversely from the package 25. However, this withdrawal is not complete until after the spindle 450 assumes the position $P_5$ in FIG. 24, by which time the first longitudinal flap 68 and central portion 66 of the package 25 have moved with the folding pin 482 to fold about the folding plate 480 and the second longitudinal flap 70, thereby forming the e-shaped pouch 26.

Figure 24:
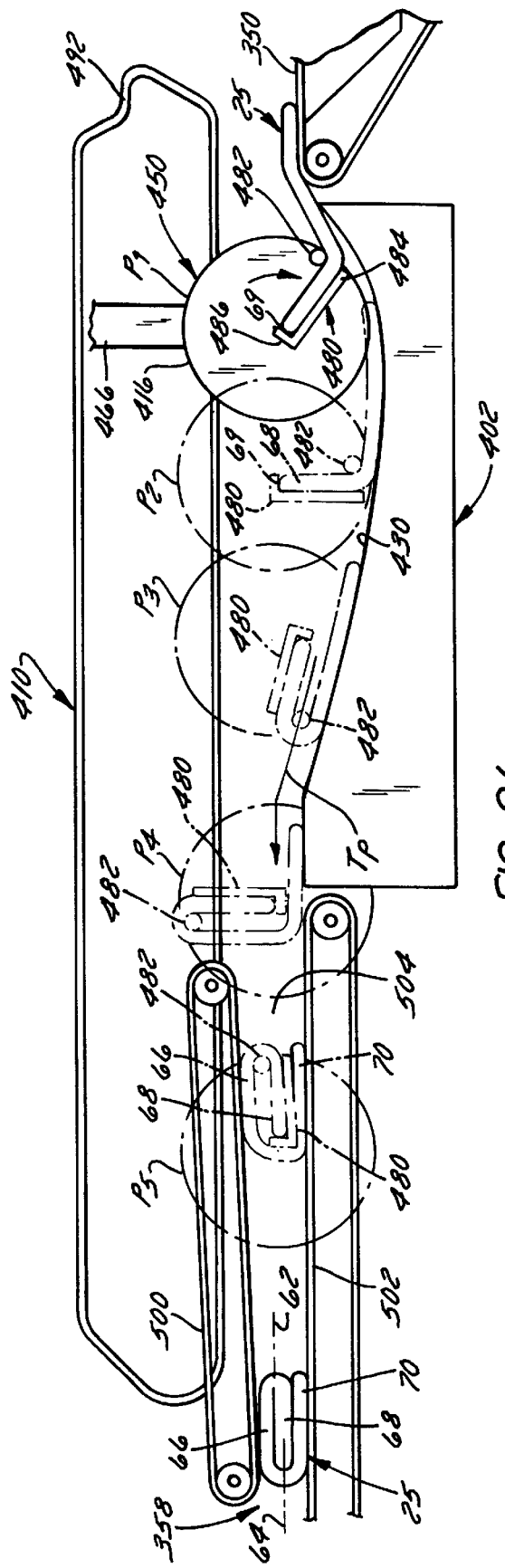
FIG. 24 is a partially schematic side elevation view of a portion of the tri-folding system of FIGS. 17 and 18 and illustrates a spool of one of the tri-folding mechanisms in various positions so as to illustrate a tri-folding operation.

The outfeed conveyor 358 has captured the e-shaped pouch 26 by this time so that it continues to convey the pouch 26 downstream or to the left in FIG. 24. Movement of the pouch 26 through the nip zone 504 formed by the converging upper and lower conveyors 500 and 502 compresses the pouch 26 to compact it and to set the pressure sensitive adhesive patch 72. The outfeed conveyor 358 then conveys the finished pouch 26 out of the wrapper/folder system 300 for subsequent action such as packaging in cartons or boxes.

Referring again to FIG. 16, after the spindle 450 of a particular tri-folding mechanism 404 is withdrawn transversely from the folded pouch 26, it is conveyed by the endless element 408 through a return stroke that extends upwardly and to the right in FIG. 16 and then downwardly and back to the left to reposition the tri-folding mechanism 404 for receiving and folding another package. During this return stroke, engagement between the guide disk 474 of the spindle 450 and the inclined section 497 of the upper portion 496 of the slot 494 in the guide track 410 forces the spindle 450 transversely back towards the vertical plane V so that the folding plate 480 and folding pin 482 may move into the travel path $T_P$ to receive another package 25 to be folded.

The above-described processes can be performed more rapidly than conventional tri-folding processes because they are performed in-line, i.e., package transfer does not have to cease or reverse directions during the folding process. In addition, because the processes do not require the operation of any conventional folding blades, there is little danger of piercing the pouch during the folding process.

Many changes and modifications could be made to the invention without departing from the spirit thereof. For instance, as mentioned previously, the invention is applicable to other absorbent articles in addition to sanitary napkins. Moreover, and within the described embodiments, the adhesive patch 72 could be eliminated or could be replaced by a strip of adhesive tape. The applicator 156 or 356 that applies the adhesive patch 72 could also be placed in a different location in the system 100 or 300, and a separate heated or ultraviolet activator could be located downstream of the two-stage folder assembly 108 or the tri-folding system 308 to set the adhesive. In addition, the two-stage folder assembly 108 of the system 100 could be inverted so that the outfeed conveyor 158 is located beneath the infeed conveyor 150 and so that the first pusher assembly 152 forces the packages 25 downwardly rather than upwardly as illustrated. The scope of other changes will become apparent from the appended claims.

We claim:

1. A method of tri-folding a package containing a wrapped absorbent article to form a pouch, said method comprising:
   a) conveying said package along a travel path;
   b) while said package travels along said travel path, rotating a tri-folding mechanism in contact with said package while translating said tri-folding mechanism at least generally along said travel path so as to
      i) fold a first longitudinal flap of said package about a central portion of said package so that said first longitudinal flap is aligned adjacent to said central portion; and ii) fold said first longitudinal flap and said central portion of said package about a second longitudinal flap of said package so that said second longitudinal flap is aligned adjacent to said first longitudinal flap; and c) releasably securing said second longitudinal flap to said first longitudinal flap to form said pouch.

2. The method of claim 1 (a) the step of folding said first longitudinal flap about said central portion comprising supporting said first longitudinal flap on a folding plate of said tri-folding mechanism while positioning a folding pin of said tri-folding mechanism in the vicinity of a lateral fold-line connecting said central portion to said first longitudinal flap, and rotating said tri-folding mechanism so that said first longitudinal flap moves with said folding plate to fold about said folding pin and said central portion, and(b) the step of folding said first longitudinal flap and said central portion of second longitudinal flap about said second longitudinal flap comprising rotating said tri-folding mechanism so that said first longitudinal flap and said central portion move with said folding pin to fold about said folding plate and said second longitudinal flap.

3. The method of claim 2 further comprising withdrawing said folding plate and said folding pin from said pouch by moving said tri-folding mechanism laterally with respect to said travel path while said tri-folding mechanism translates at least generally along said travel path.

4. The method of claim 3 the step of moving said tri-folding mechanism laterally comprising engaging a surface of said tri-folding mechanism with a cam that forces said tri-folding mechanism to move at an acute angle away from said travel path.

5. The method of claim 4 said cam comprising an inclined surface of a slot of a guide track for said tri-folding mechanism.

6. The method of claim 1 said travel path extending at least generally along a vertical plane, said method further comprising a) supporting said tri-folding mechanism on a support track which extends at least generally in parallel with said vertical plane and which is spaced transversely from said vertical plane, and b) guiding at least a portion of said tri-folding mechanism along a guide track which extends at least generally in parallel with said vertical plane and which is positioned between said vertical plane and said support track.

7. The method of claim 6 further comprising driving said portion of said tri-folding mechanism to move transversely with respect to said vertical plane via engagement with an inclined edge surface of said guide track.

8. The method of claim 6 the step of rotating said tri-folding mechanism in contact with said package while translating said tri-folding mechanism along said travel path comprising a) driving said tri-folding mechanism to move at least generally in parallel with said vertical plane using an endless drive element which extends in parallel with said vertical plane and which is disposed between said support track and said guide track, and b) driving said tri-folding mechanism to rotate using an electric motor which is supported on said endless drive element and which has an output shaft extending transversely with respect to said vertical plane.

9. The method of claim 1 the step of releasably securing comprising bonding said first and second longitudinal flaps together.

10. The method of claim 9 the bonding step comprising applying an adhesive to at least one of said first and second longitudinal flaps and pressing said first and second longitudinal flaps together after the application of said adhesive.

11. A method of folding a package containing a wrapped absorbent article to form a pouch, said package containing a wrapped absorbent article, said method comprising:

a) simultaneously translating a tri-folding mechanism at least generally along a travel path and rotating said tri-folding mechanism, said travel path extending in a vertical plane, said tri-folding mechanism comprising a rotatable spindle which has an axis of rotation extending transversely with respect to said vertical plane, an electric motor which drives said spindle to rotate, an at least generally L-shaped folding plate which is mounted on an axial face of said spindle and which extends axially away from said axial face, and a folding pin which is mounted on said axial face and which extends axially away from said axial face, said spindle being driven along said travel path by an endless chain, being supported on a slotted support track, and being guided by a slotted guide track;

b) positioning said package in a location in which a first longitudinal flap of said package is located between said folding plate and said folding pin and is supported on said folding plate, and in which said folding pin is located in the vicinity of a lateral fold-line connecting said central portion to said first longitudinal flap; then c) continuing to rotate said tri-folding mechanism while translating said tri-folding mechanism in parallel with said vertical plane so that said first longitudinal flap moves with said folding plate to fold about said folding pin and said central portion; then d) continuing to rotate said tri-folding mechanism while driving said tri-folding mechanism at least generally in parallel with said vertical plane so that said first longitudinal flap and said central portion move with said folding pin to fold about said folding plate and said second longitudinal flap to form said pouch;

e) driving said tri-folding mechanism to move at an acute angle with respect to said vertical plane so that said folding plate and said folding pin withdraw from said pouch, said tri-folding mechanism rotating 360° during the steps c), d), and e); and f) bonding said first and second longitudinal flaps together.

12. A method comprising:

a) providing an absorbent article which has first and second major mutually opposed faces;

b) providing a wrapper having an absorbent article-receiving surface; then c) releasably securing at least a portion of said first face of said absorbent article to said absorbent article-receiving surface of said wrapper to form an assembly, said assembly having a longitudinal centerline, a lateral centerline, and a perimeter, said perimeter being formed from a pair of opposed lateral edges disposed on opposite sides of said longitudinal centerline and a pair of opposed longitudinal ends disposed on opposite sides of said lateral centerline;

d) folding said lateral edges longitudinally over said second face of said absorbent article to encase said absorbent article;

e) releasably securing said lateral edges to one another to form a package;

f) conveying said package along a travel path;

g) while said package travels along said travel path, rotating a tri-folding mechanism in contact with said package while translating said tri-folding mechanism at least generally along said travel path so as to
  i) fold a first longitudinal flap of said package over a central portion of said package so that said first longitudinal flap is aligned adjacent to said central portion, and
  ii) fold said first longitudinal flap and said central portion of said package over a second longitudinal flap of said package so that said second longitudinal flap is aligned adjacent to said first longitudinal flap; and
h) releasably securing said second longitudinal flap to said first longitudinal flap.

13. A system for forming a pouch by the in-line folding of a package, containing a wrapped absorbent article said system comprising:
  a) a package support structure defining a travel path for movement of said package through said system; and
  b) a tri-folding mechanism which is rotatable and which is translatable with respect to said travel path, said tri-folding mechanism being adapted to engage and tri-fold said package as said package moves along said travel path.

14. The system of claim 13 said package support structure comprising a stationary guide surface.

15. The system of claim 13 said tri-folding mechanism including first and second spaced-apart folding elements which are adapted to engage mutually opposed major faces of said package.

16. The system of claim 15 said first and second folding elements comprising an L-shaped folding plate and a cylindrical folding pin, respectively.

17. The system of claim 15 said tri-folding mechanism further comprising a rotatable support structure on which said first and second folding elements are mounted.

18. The system of claim 17 said rotatable support structure comprising a spindle having an axial face on which said first and second folding elements are mounted.

19. The system of claim 17 said tri-folding mechanism further comprising a motor which drives said rotatable support structure to rotate.

20. The system of claim 17 said travel path extending at least generally in a vertical plane, and further comprising an endless drive element which drives said rotatable support structure to move at least generally in parallel with said vertical plane, said tri-folding mechanism comprising a linkage which couples said rotatable support structure to said endless drive element and which permits said rotatable support structure to move transversely relative to said vertical plane.

21. The system of claim 20 further comprising a support track on which said linkage and said rotatable support structure are movably supported.

22. The system of claim 17 further comprising a guide structure which guides said rotatable support structure as said rotatable support structure moves along said travel path, a portion of said guide structure acting as a cam which forces said rotatable support structure to move laterally with respect to said travel path at designated locations along said travel path.

23. The system of claim 22 said guide structure comprising a guide track having a slot which guides said rotatable support structure, and said portion of said guide structure comprising an inclined edge surface of said slot.

24. A system for forming a pouch by the in-line folding of an individually wrapped and packaged absorbent article, said system comprising:
  a) a stationary guide surface which defines a travel path for movement of said wrapped and packaged absorbent article through said system;
  b) an endless chain which is positioned above said guide surface, which extends in parallel with a vertical plane extending through said travel path, and which is spaced transversely from said vertical plane;
  c) a guide track which extends in parallel with said endless chain and said vertical plane and which is positioned between said vertical plane and said endless chain, said guide track having a generally ovoid slot formed therein having upper end lower portions;
  d) a support track which extends in parallel with said endless chain such that said endless chain is positioned between said guide track and said support track, said support track having a generally ovoid slot formed therein having upper and lower portions; and
  e) a plurality of tri-folding mechanisms which are spaced along said endless chain, which are supported by said support track, and which are guided by said guide track, each of said tri-folding mechanisms comprising
    i) a roller which is rotatably supported in said slot of said support track;
    ii) a linkage which is rotatably attached to said roller and which extends transversely with respect to said vertical plane from said roller, towards said vertical plane, past said endless chain, and towards said guide track, said linkage being attached to said endless chain;
    iii) a motor which is mounted on said linkage and which has a rotatable output shaft extending transversely with respect to said vertical plane;
    iv) a spindle which has an axis of rotation extending transversely with respect to said vertical plane, which has an axial guide face captured in said slot of said guide track, and which has an axial support face spaced axially from said guide face;
    v) a splined coupling via which said spindle is attached to said output shaft of said motor so as to permit relative axial motion therebetween while prohibiting relative rotational motion therebetween;
    vi) an L-shaped folding plate which is affixed to said guide face of said spindle and which extends transversely towards said vertical plane; and
    vii) a cylindrical folding pin which is affixed to said guide face of said spindle, which is spaced from said folding plate, and which extends transversely towards said vertical plane.

25. A system comprising:
  a) an assembly former which releasably secures absorbent articles to a continuous sheet of wrapper material to form assemblies;
  b) a longitudinal folder which is located downstream of said assembly former and which folds said continuous sheet longitudinally over said absorbent articles;
  c) a cutter which is located between said longitudinal folder and said first conveyor and which cuts said continuous sheet between said absorbent articles to form packages; and
  d) a system for tri-folding said packages to form pouches, said system including
    i) an article support structure defining a travel path for movement of said packages through said system; and
    ii) a tri-folding mechanism which is rotatable and which is translatable with respect to said travel path, said tri-folding mechanism being adapted to engage and tri-fold said packages as said packages moves along said travel path.

* * * * *